United States Patent

Ferres et al.

[11] 4,036,829
[45] July 19, 1977

[54] LACTONYL ESTERS OF PENICILLINS

[75] Inventors: Harry Ferres; John Peter Clayton, both of Horsham, England

[73] Assignee: Beecham Group Limited, England

[21] Appl. No.: 712,821

[22] Filed: Aug. 5, 1976

Related U.S. Application Data

[63] Continuation of Ser. No. 524,776, Nov. 18, 1974, abandoned, which is a continuation of Ser. No. 259,941, June 5, 1972, abandoned.

[30] Foreign Application Priority Data

June 9, 1971 United Kingdom ............... 19604/71

[51] Int. Cl.$^2$ ................. C07D 499/44; C07D 499/46; C07D 499/48; C07D 499/64
[52] U.S. Cl. ............................. 260/239.1; 260/243 C; 424/271; 424/246
[58] Field of Search ....................................... 260/239.1

[56] References Cited

U.S. PATENT DOCUMENTS

| | | | |
|---|---|---|---|
| 2,985,648 | 5/1961 | Doyle et al. | 260/239.1 |
| 3,641,001 | 2/1972 | Love et al. | 260/239.1 |
| 3,647,783 | 3/1972 | Pirie | 260/239.1 |
| 3,697,507 | 10/1972 | Frederiksen et al. | 260/239.1 |
| 3,860,579 | 1/1975 | Ferres et al. | 260/239.1 |

FOREIGN PATENT DOCUMENTS 1,377,661 12/1974 United Kingdom .............. 260/239.1

Primary Examiner—Gerald A. Schwartz
Attorney, Agent, or Firm—Jacobs & Jacobs

[57] ABSTRACT

Lactonyl esters of Penicillins of the formula

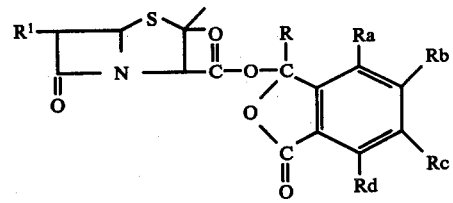

wherein $R^1$ is an antibacterially active penicillin-completing side chain; R is hydrogen, methyl or phenyl; and Ra, Rb, Rc, Rd are hydrogen, lower alkyl, lower alkoxy, halo, and nitro, provided that when R is hydrogen and $R^1$ is D-α-aminophenylacetamido and Ra, Rb, Rc, and Rd are not all hydrogen are disclosed to possess antibacterial properties.

37 Claims, No Drawings

LACTONYL ESTERS OF PENICILLINS

CROSS-REFERENCE

This is a continuation, of Ser. No. 524,776 filed Nov. 18, 1974 which is a continuation of Ser. No. 259,941, filed June 5, 1972, both now abandoned.

This invention relates to a novel class of esters of penicillins and cephalosporins which, upon oral administration are absorbed into the bloodstream where they are split by enzymic action to release the antibacterially active parent penicillin or cephalosporin.

According to the present invention there is provided a class of compounds of formula I:

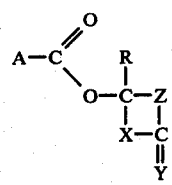

wherein
X and Y are the same or different and each represents oxygen or sulphur;
Z represents the residue of a lactone, thiolactone or dithiolactone ring system;
R represents hydrogen or an alkyl, alkenyl, alkynyl, aryl or aralkyl group, or a functional substituent;
A represents a group of formula II or (III):

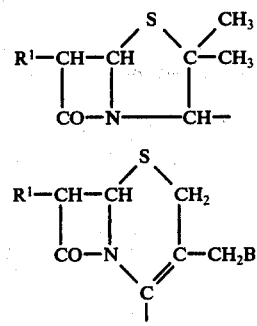

wherein B represents hydrogen, an acetoxy group or a pyridinium group and $R^1$ is an organic acylamino group, a group of formula IV:

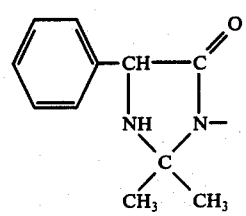

or a group of formula (V):

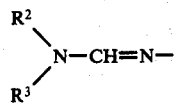

wherein $R^2$ and $R^3$ each represent a lower alkyl group, or $R^2$ and $R^3$ taken together with the nitrogen atom to which they are attached form a monocyclic ring.

By way of example, in formula (I) above Z may be a straight or branched, saturated or unsaturated divalent hydrocarbon radical carbon atoms, and two or more carbon atoms in the radical may be joined in a carbocyclic or heterocyclic ring system. The radical Z may also carry one or more functional substituents such as hydroxy, alkoxy, halogen, nitro, amino or carboxyl groups. Specifically, Z may be a 1,2-phenylene group which may carry one or more substituents such as alkoxy, nitro or halogen substituents.

Also by way of example, the group R in formula (I) above may be lower alkyl, e.g. methyl or ethyl; lower alkenyl, e.g. vinyl or allyl; lower alkynyl e.g. ethynyl; aryl e.g. phenyl; or aralkyl e.g. benzyl. R may also be a functional group such as a hydroxy, alkoxy, halogen, amino or carboxyl group.

The radical A in formula (I) is a 6-substituted penam or cephem radical. When $R^1$ is an organic acylamino group, any of the acylamino side chains found in known antibacterially active penicillins and cephalosporins are suitable. For example, $R^1$ in formulae II or III may by phenylacetamido; 2- or 2-thienylacetamido; phenoxyacetamido, α-amino-phenylacetamido; α-amino-2(or 3-) thienylacetamido, α-carboxyphenylacetamido; α-sulphophenylacetamido; α-azidophenylacetamido or α-guanidinophenylacetamido, but other examples of suitable acylamino groups will be found later in this specification in the specific examples.

It will be clear that when the acylamino group $R^1$ contains an asymmetric carbon atom, the compounds of this invention can exist in two optically active forms. This invention includes the pure epimers as well as mixtures of epimers.

In formulae (II) and (III) $R^1$ may also be a group of formula (V). Preferably $R^2$ and $R^3$ in formula (V) are both methyl or together represent the divalent radical — $CH_2(CH_2)_4CH_2$—.

In the presence of human and animal serum, the esters of this invention are split to release the parent penicillanic or cephalosporanic acid. Although this invention is not limited by any theory of mechanism, we believe that non-specific esterases in the serum split the molecule to give an unstable intermediate (VI):

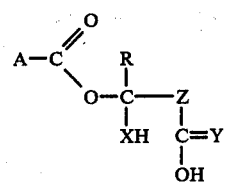

The intermediate (IV) then undergoes spontaneous decomposition as follows:

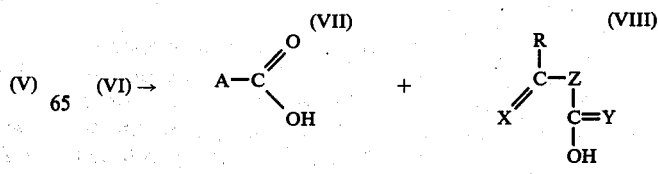

The esters of this invention may be prepared by esterification of the carboxyl group of the corresponding penicillanic acid or cephalosporanic acid.

Thus, the invention also provides a process for the preparation of compounds (I) which process comprises reacting a compound of formula (IX)

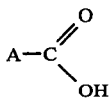
(IX)

or a reactive esterifying derivative thereof, in which formula A is as defined with respect to formula (I) with a compound of formula (X).

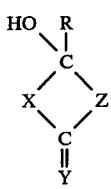
(X)

or a reactive esterifying derivative thereof, in which formula X, Y, Z and R are as defined in formula (I).

By the term "reactive esterifying derivative" in relation to compounds (IX) and (X) above, we mean derivatives of (IX) and (X) which when reacted together take part in a condensation reaction with the consequent formation of an ester linkage:

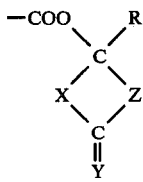

Many methods of esterification using several different combinations of reactive esterifying derivative are known from the literature. For example, the esterification reaction defined above may be achieved by reacting a compound of formula (1 X A)

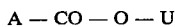
A — CO — O — U         (1 X A)

wherein A is as defined with reference to formula (I) above, with a compound of formula (XA)

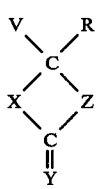
(XA)

wherein R, X, Y and Z are as defined in relation to formula (I), under conditions which cause the elimination of the elements of compound UV with the consequent formation of the ester of formula (I); the symbols U and V in formulae (1 X A) and (XA) being such that U represents hydrogen or a salt-forming ion and V represents a hydroxy group, an alkylsulphonyloxy group, an arylsulphonyloxy group or a halogen atom; or represents an organic acyl group and V represents a hydroxy group, an alkyl-sulphonyloxy groups or an arylsulphonyloxy group.

When the group $R^1$ in radical A of compound (IX) contains a free amino group, it is preferable that the amino group should be protected prior to the esterification reaction. More will be said about specific protecting groups which can be employed later.

The esterification procedures outlined above are all specific applications of esterification methods known in the literature. Usually it will be found satisfactory to react compound (IXA) wherein U is a sodium or potassium ion; with compound (XA) wherein V is a halogen atom, especially bromine or chlorine.

When U in compound (IXA) is hydrogen or a salt-forming ion and V in compound (XA) is a hydroxy group, the reaction is generally slow and inconvenient. Preferably, in such cases the hydroxy group V in compound (XA) is best converted to an alkylsulphonyl or arylsulphonyl ester (especially the p-toluene sulphonate), since this gives a smoother reaction. In this case, the presence of a base is usually necessary to achieve high yields.

In the case where the group U in reagent (IXA) is an organic acyl group, it will be clear that (IXA) is simply a mixed anhydride, the acyl group may be one of a wide variety of aliphatic or aromatic acyl groups but generally the alkoxy carbonyl groups (e.g. $C_2H_5OCO-$ group) are satisfactory. Again, when a mixed anhydride reagent (IXA) is used, the group V in reagent (XA) may be hydroxy, or an alkylsulphonyloxy or arylsulphonyloxy group.

Another reactive esterifying derivative of compound (IX) above is the acid halide, particularly the acid chloride. This compound may be reacted with the hydroxy compound (X) or an alkylsulphonyl ester thereof (e.g. the p-toluene sulphonate) in the presence of an acid binding agent to prepare the desired ester of this invention.

When the group $R^1$ in radical A of compound (IX) or (IXA) contains a free amino group, this group should be protected before the esterification reaction.

Examples of protected amino groups include the protonated amino group ($NH_3^+$) which after the acylation reaction can be converted to a free amino group by simple neutralisation; the benzyloxycarbonylamino group (X = $NH.CO_2CH_2Ph$) or substituted benzyloxycarbonylamino groups which are subsequently converted to $NH_2$ by catalytic hydrogenation; and various groups which after the acylation reaction regenerate the amino group on mild acid hydrolysis. (Alkaline hydrolysis is not generally useful since hydrolysis of the ester group takes place under alkaline conditions).

Examples of the group X which may subsequently be converted to $NH_2$ by mild acid hydrolysis include anamine groups of general formula (XI) or tautomeric modifications thereof, and α-hydroxyarylidene groups of general formula (XII) or tautomeric modifications thereof:

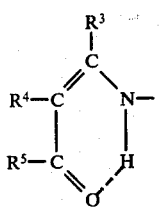 (XI)

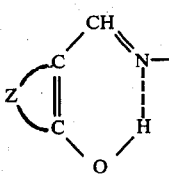 (XII)

In structures (XI) and (XII) the dotted lines represent hydrogen bonds. In structure (XI) $R^3$ is a lower alkyl group, $R^4$ is either a hydrogen atom or together with $R^3$ completes a carbocyclic ring, and $R^5$ is a lower alkyl, aryl, or lower alkoxy group. In structure (XII) X represents the residue of a substituted or unsubstituted benzene or naphthalene ring.

An example of a "protected amino" which can be converted to $NH_2$ after the esterification reaction is the azido group. In this case, the final conversion into $NH_2$ may be brought about by either catalytic hydrogenation or electrolytic reduction.

An alternative method of making compounds of this invention of formula (I) wherein the $R^1$ group in radical A is an acylamino group, is by N-acylation of the corresponding 6-aminopenam or 7-aminocephem.

Thus, in another of its embodiments, this invention provides a method for the preparation of compounds of formula (I) wherein the group $R^1$ is radical A is an acylamino group, which method comprises reacting a compound of formula (XII)

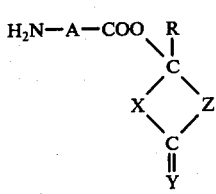 (XII)

or a silyl derivative thereof with a reactive N-acylating derivative of a compound of formula (XIII)

$R_a^1 OH$ (XIII)

wherein $R_a^1$ is an organic acyl group which may carry a protected amino group, removing the silyl group, if present, by hydrolysis or alcoholysis, and, if a protected amino group is present, optionally converting it to a free amino group under acid or neutral conditions.

By the term "silyl derivative" of the compound (XII) we mean the product of the reaction between compound (XII) and a silylating agent such as a halotrialkylsilane, a dihalodialkylsilane, a halotrialkylsilane, a dihalodialkoxysilane or a corresponding aryl or aralkyl silane and compounds such as hexamethyldisilazane. In general halotrialkylsilanes are preferred, especially trimethylchlorosilane. The silylated derivatives of the ester (XII) are extremely sensitive to moisture and hydroxylic compounds, and after reaction with the reactive derivative of compound (XIII), the silyl group of the intermediate acylated compound can be removed by hydrolysis or alcoholysis.

A reactive N-acylating derivative of the acid (XIII) is employed in the above process. The choice of reactive derivative will of course be influenced by the chemical nature of the acyl group $R^1$. Thus, when $R^1$ is acid stable or carries an acid stable group, such as the protonated amino group $NH_3^+$ or the azido group, it is often convenient to convert the acid (XIII) into an acid halide for example by treating it with thionyl chloride or phosphorus pentachloride to give the acid chloride.

Such reagents would however be avoided when $R^1$ is an acid labile group or carries an acid labile group, e.g. of type (XI) or (XII). In such cases it is often convenient to make use of a mixed anhydride. For this purpose particularly convenient mixed anhydrides are the alkoxyformic anhydrides, which are conveniently prepared by treating an alkali metal or tertiary amine salt of the acid (XIII) with the appropriate alkyl chloroformate in an anhydrous medium at or below room temperature.

Other reactive N-acylating derivatives of the acid (XIII) include the reactive intermediate formed on reaction in situ with a carbodiimide or carbonyldiimidazole.

The ester (XIII) used in the above process can be prepared, though in poor yield by direct coupling of 6-amino-penicillanic or 7-amino cephalosporanic acid with 3-bromophthalide in the presence of base. With this process some epimerisation at $C_6$ or $C_7$ occurs and the process is therefore not entirely satisfactory.

The esters of formula (XIII) are also new compounds and, since they are valuable intermediates in the process of this invention, they also form part of the invention. Much better yields of compounds (XIII) acid phthalide ester can be achieved by coupling an N-protected derivative of 6-aminopenicillanic acid or 7-amino cephalosporanic acid (e.g. the triphenylmethyl derivative) with 3-bromophthalide and thereafter removing the protecting group (e.g. by mild acid hydrolysis in the case of the triphenylmethyl derivative).

Alternative types of N-protected 6-amino penicillanic acid are the 6-acyl-aminopenicillanic acids. Techniques for the removal of the 6-acyl side chain from benzylpenicillin and phenoxymethyl penicillin, for example, are well documented (cf. British Pat. No. 1,189,022) and generally involve treating an ester of the 6-acylainopenicillanic acid with $PCl_5$ to form an imino chloride bond on the 6-amido nitrogen atom, then treating the imino chloride with an alcohol to form an imino ether and then hydrolysing the imino bond to form the 6-aminopenicillanic acid ester. In the present case, it is possible to start from the phthalide ester of penicillin G or penicillin V (prepared for example by reaction of the sodium or potassium salt of the penicillin with 3-bromo phthalide) and cleave and acyl side chain to prepare the phthalide ester of 6-aminopenicillanic acid.

Similarly, alternative types of N-protected 7-amino cephalosporanic acid are the 7-acylaminocephalosporanic acids. Techniques for the removal of the 7-acyl side chain from cephalosporins are well known, and in the present case, it is possible to start with the appropriate ester of a 7-acylamino cephem, e.g. Cephalosporin C and remove the acyl side chain to form the ester of 7-aminocephalosporanic acid.

The following Examples illustrate methods for the preparation of some of the compounds of this invention.

EXAMPLE 1 a. PREPARATION OF 5,6-DIMETHOXY-PHTHALIDE METHOD 1.

3,4-dimethoxybenzoic acid (12.5 g.; 0.0687 mole) was heated on a water bath for 12 hours with formaldehyde solution (37 – 41%; 13.75 ml.) and conc. hydrochloric acid (50 ml.).

The black mixture was diluted with its own volume of water, cooled and shaken and the suspension decanted from the black oil deposited on the sides of the flask. The decanted liquid was left overnight to crystallise. The solid was filtered, washed with water and recrystallised from ethanol (Yield 4.5 g.).

The black oily residue in the reaction vessel was extracted with hot sodium hydroxide solution, treated with charcoal and acidified with hydrochloric acid, cooled and left to crystallise. The solid was filtered, washed with water and recrystallised from ethanol (Yield 1.6 g.).

Total Yield 6.1 g. 45.8%
M.P. 155° – 6° C (Lit. 155° – 7° C)

METHOD 2

3,4-Dimethoxybenzoic acid (100 g; 0.55 mole.) was heated with formaldehyde solution (37 – 41%; 256 ml.) and conc. hydrochloric acid (836 ml.) on a water bath with efficient stirring for 2 hours.

The black liquid was allowed to cool and was decanted from a small amount of black solid, into water (5 lits.). The solid was filtered off, washed with sodium carbonate solution and then with water, dried and recrystallised from ethanol.

Yield 41.2 g. 38.6%

This method has the advantage of being quicker and of producing less tarry material than method 1, although yields are somewhat lower.

I.R. Spectrum (Nujol) shows following strong bands: 1750 cm$^{-1}$ (wide) 1600 cm$^{-1}$ 1500 cm$^{-1}$ 1335 cm$^{-1}$ 1295 cm$^{-1}$ 1125 cm$^{-1}$ 1045 cm$^{-1}$ 768 cm$^{-1}$ N.M.R. Spectrum (CD$_3$)$_2$SO) shows following peaks:
$\delta$ = 7.26 (2H.d) Aromatic protons
$\delta$ = 5.30 (2H.s) Phthalide — CH$_2$
$\delta$ = 3.90 (6H.d) Methoxy — protons b. PREPARATION OF 3-BROMO-5,6-DIMETHOXY-PHTHALIDE 5,6-Dimethoxyphthalide (5.82 g; 0.03 mole.), N-bromosuccinimide (5.34 g; 0.03 mole.) and α-azoisobutyronitrile (0.1 g.) were gently refluxed in dry carbon tetrachloride (150 ml.) for 2 hours.

The solution was cooled, the succinimide filtered off and the solvent removed in vacuo leaving a yellow solid, which was washed with 40° – 60° petrol, and dried.

This solid was used immediately and not stored as it is unstable in moist air.

Yield 7.6 g. 93% c. 6[D(—) α-aminophenylacetamido] penicillanic acid, 5,6-dimethoxy-phthalide ester, hydrochloride.

Potassium salt of 6[D(—)N-(1-methoxycarbonylpropen-2-yl)-α-aminophenyl-acetamido] penicillanic acid (10.7 g; 0.0212 mole.) and 3-bromo-5,6-dimethoxyphthalide (5.8 g; 0.021 mole.) were stirred overnight in any acetone (200 ml). The mixture was filtered through Celite and evaporated in vacuo to a foam.

The foam was dissolved in ethyl acetate (210 ml.) and washed with N/2 sodium bicarbonate solution (70 ml.), water (70 ml.) and saturated brine (2 × 70 ml.). The solution was again evaporated in vacuo to a foam.

The foam was dissolved in acetone (105 ml.) and water (70 ml.) added and the pH maintained at 1.9 on the pH-meter by dropwise addition of 5N hydrochloric acid (3.9 ml.). The acetone was removed from the clear solution by evaporation in vacuo and the resultant aqueous liquid extracted with ethyl acetate (105 ml.). The organic layer, on separation, was diluted with 40°-60° petrol (75 ml.) and extracted with water at pH 3.0 (30 ml.).

The combined aqueous extracts were treated with solid sodium chloride (35 g.) and stirred for 1 hour. The resulting oil was separated, dissolved in acetone (120 ml.), dried over anhydrous magnesium sulphate and filtered into stirring, dry, ether (3 lits.)

The precipitated solid was filtered, washed with dry ether and sucked dry to yield the ester as a fine, white electrostatic powder.

| YIELD: | 3.5g. (28.6%). | | | | | |
|---|---|---|---|---|---|---|
| ANALYSIS: | C | H | N | O | S | Cl. |
| required: | 54.03 | 4.85 | 7.27 | 22.16 | 5.54 | 6.15 |
| found: | 51.19 | 4.77 | 6.97 | — | 5.37 | 6.06 |

I.R. SPECTRUM: Strong bands at 1790 cm$^{-1}$ 1695 cm$^{-1}$ 1602 cm$^{-1}$ 1500 cm$^{-1}$ 1340 cm$^{-1}$ 1288 cm$^{-1}$ 1128 cm$^{-1}$ 978 cm$^{-1}$.

N.M.R. SPECTRUM: (CD$_3$)$_2$SO: $\delta$ = 1.43(6H.d. gem dimethyls) 3.92(6H.s. CH$_3$O-protons) 4.49(1H.s. C$_3$ proton) 5.15(1H.m. α-proton) 5.54(2H.m. β-lactams) 7.42(8H.m. phenyl aromatics, phthalide aromatics, phthalide 3-proton) 9.6–8.5(4H. two diffuse peaks, removable on addition of D$_2$O. —CONH—; —NH$_3^+$).

a. 6-Methoxyphthalide

6-Methoxyphthalide was prepared by the reaction of m-anisic acid with formaldehyde solution and conc. hydrochloric acid by the method of Chakravarti and Perkin, J. Chem. Soc., 1929, 199, except that heating was only continued till all solid had dissolved, not for as long as 1 hour. Further reaction time was found to result in substitution in the phthalide 5-position.

Yield 13%

M.P. 120° C (Lit. 120° C)

I.R. (Nujol) Strong bands at: 1755 cm$^{-1}$ 1490 cm$^{-1}$ 1378 cm$^{-1}$ 1328 cm$^{-1}$ 1280 cm$^{-1}$ 1059 cm$^{-1}$ 998cm$^{-1}$ 778 cm$^{-1}$ N.M.R. [(CD$_3$)$_2$SO]
$\delta$ = 3.88 (3 H. S. —OCH$_3$)
$\delta$ = 5.37 (2 H. S. phthalide —CH$_2$—)
$\delta$ = 7.48 (3 H. m. phthalide crometics)

b. 3-Bromo-6-methoxyphthalide

3=Bromo-6-methoxyphthalide was prepared using the same procedure as described in Example 1 (b).

c. 6[D(—)α-aminophenylacetamido]penicillanic acid 6-methoxyphthalide ester, hydrochloride The potassium salt of 6[D(—)N-(1-methoxycarbonyl-propen-2-yl)-α-aminophenylacetamido]penicillanic acid (15.5 gm, 0.0308 mole) and 3-bromo-6-methoxyphthalide (7.5 gm; 0.0308 mole) were stirred overnight in dry acetone (200 ml.). The mixture was filtered throught Celite and evaporated in vacuo to a foam, which was dissolved in ethyl acetate (210 ml.) and washed with n/2 sodium bicarbonate solution (70 ml.), water (70 ml.) and saturated brine (2 × 70 ml.). The solution was again evaporated to a foam in vacuo and then dissolved in acetone (105 ml.) and water (70 ml.) added. The pH was then maintained at ca. 1.9 on the pH meter by dropwise addition of 5N hydrochloric acid (4.9 ml.). The acetone was removed from the clear solution in vacuo and the aqueous layer extracted with ethyl acetate (105 ml.).

The aqueous layer was treated with solid sodium chloride (25.9 gm) and stirred for one-half hour. The resultant oil was separated and dissolved in isopropanol (38 ml.) dried over anhydrous magnesium sulphate, filtered and poured slowly with stirring into dry ether (3 liters). The precipitated solid was filtered, washed with ether and dried.

Yield 9.9 gms. 58.5%
Hydroxylamine Assay 119.1%

| Analysis | C | H | N | O | S | Cl |
|---|---|---|---|---|---|---|
| $C_{25}H_{26}N_3O_2SCl$ | | | | | | |
| Requires % | 54.79 | 4.75 | 7.67 | 20.46 | 5.85 | 6.48 |
| Found % | 51.97 | 4.61 | 7.11 | — | 4.88 | 6.29 |
| | — | — | — | — | 4.99 | 6.60 |

I.R. Spectrum (KBr disc) shows the following inter alia strong bands:
1780 cm$^{-1}$ 1670 cm$^{-1}$ 1497 cm$^{-1}$ 1321 cm$^{-1}$ 1284 cm$^{-1}$ 1246 cm$^{-1}$ 1149 cm$^{-1}$ 976 cm$^{-1}$ N.M.R. Spectrum [(CD$_3$)$_2$SO]
δ = 1.41 (6H. d. Gem-dimethyls)
δ = 3.90 (3H. s. Methoxy-protons)
δ = 4.49 (1H. s. C$_3$ proton)
δ = 5.18 (1H. broad s. α-proton)
δ = 5.52 (2H. m. β-lactams)
δ = 7.49 (9H. m. phenyl aromatics phthalide aromatics phthalide C$_3$ proton)
δ = 8.7 - 9.1 (3H. m. removable on D$_2$O exchange —NH$_3$$^+$)
δ = 9.2 - 9.4 (1H. m. removable on D$_2$O exchange CONH)

EXAMPLE 3 a. 6-Chloro-Phthalide

Prepared by the action of sulphuryl chloride on phthalide in a melt of aluminium chloride (anhydrous) and sodium formate as in the German Pat. No. 1,266,310.

b. 3-Bromo-6-Chloro-phthalide

6-Chlorophthalide (7.66 gms; 0.0452 mole), N-bromosuccinimide (8.1 gms; 0.0452 mole) and azobisbutyronitrile (0.1 gm) were gently refluxed in dry carbon tetrachloride (150 ml.) for 1½ hours. On cooling, the succinimide was filtered off and the solvent removed in vacuo to leave a yellow solid, which was used immediately. Yield 9.57 gms. 86.2% c. 6[D(—)α-aminophenylacetamido]penicillanic acid 6-chloro-phthalide ester, hydrochloride 6[D(—)N-(1-methoxycarbonylpropen-2-yl)-α-aminophenylacetamido] penicillanic acid, potassium salt (22.9 gms; 0.0455 mole) and 3-bromo-6-chlorophthalide (11.24 gms; 0.0455 mole) in dry acetone (350 ml.) were stirred overnight.

The mixture was filtered through Celite and the solution evaporated in vacuo to a foam. The foam was dissolved in ethyl acetate (250 ml.) and washed with N/2 sodium bicarbonate (100 ml.), water (100 ml.) and saturated brine (100 ml.), and dried over anhydrous magnesium sulphate.

The solution was concentrated to ca. 50 ml. in vacuo and poured into vigorously stirring 40°-60° petrol(3 lit.). The solid was filtered, washed with petrol and dried, giving the 6-chloro-phthalide ester of 6[D(—)N-(1-methoxycarbonylpropent-2-yl)-α-aminophenyl acetamido] penicillanic acid as a light yellow solid.

Yield 15.3 gms. 55.8%

I.R. Spectrum (KBr disc) shows the following inter alia strong bands:
1782 cm$^{-1}$ 1685 cm$^{-1}$ 1657 cm$^{-1}$ 1599 cm$^{-1}$ 1292 cm$^{-1}$ 1265 cm$^{-1}$ 1170 cm$^{-1}$ 1080 cm$^{-1}$ N.M.R. Spectrum ( (CD$_3$)$_2$SO) shows the following peaks:

N.M.R. Spectrum ((CD$_3$)$_2$SO) shows the following peaks:
δ = 1.49 (6H. m. Gem-dimethyls)
δ = 1.78 (3H. s. CH$_3$ in the enamine ring.)
δ = 3.56 (3H. s. —OCH$_3$)
δ = 4.51 (1H. s. C$_3$ proton)
δ = 4.55

(1H. s. 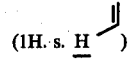 )

δ = 5.55 (3H. m. β-lactams and α-proton).
δ = 7.38 (5H. s. phenyl aromatics)
δ = 7.58 (1H. s. phthalide C$_3$ proton)
δ = 7.92 (3H. m. phthalide aromatics)
δ = 9.0 - 9.5 (2H. removable with D$_2$O.

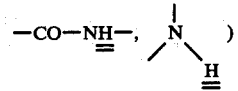 )

| Analysis for $C_{29}H_{28}N_3O_8SCl$ | | | | |
|---|---|---|---|---|
| C | H | N | S | Cl |
| Required % 56.73 | 4.56 | 6.85 | 5.22 | 5.79 |
| Found % 55.55 | 4.45 | 6.72 | 4.47 | 6.71 |
| 55.94 | 4.51 | 6.83 | 4.28 | 6.47 |

This ester was dissolved in acetone (175 ml.) and water (150 ml.) added. The pH was maintained at 1.8 on the pH meter by dropwise addition of 5N hydrochloric acid. The acetone was removed in vacuo and the aqueous solution extracted with ethyl acetate (30 ml.). The aqueous solution was then salted with solid sodium chloride and the resulting oil separated, dissolved in acetone (50 ml.) and dried over anhydrous magnesium sulphate. The solution was poured into vigorously stirring dry ether (3 lit.) and the solid filtered, washed with ether and dried to give the 6-chlorophthalide ester of 6-(D(—)-α-aminophenylacetamido)penicillanic acid, hydrochloride.

Yield 6.4 gms, 46.5%
Hydroxylamine Assay 109.8%

I.R. Spectrum (KBr disc) shows the following inter alia strong bands:
1780 cm$^{-1}$ 1684 cm$^{-1}$ 1294 cm$^{-1}$ 1209 cm$^{-1}$ 1050 cm$^{-1}$ 982 cm$^{-1}$ 700 cm$^{-1}$ N.M.R. Spectrum ( (CD$_3$)$_2$SO) shows the following peaks:

δ = 1.43 (6H. d. Gem-dimethyls)
δ = 4.53 (1H. s. C$_3$-proton)
δ = 5.19 (1H. broad S, sharpening with D$_2$O, α-proton)
δ = 5.52 (2H. m. β-lactams)

δ = 7.52 (6H. m. phenyl aromatics, phthalide C₃ proton)
δ = 7.94 (3H. m. phthalide aromatics)
δ = 9.05 (3H. broad band removable with D₂O —NH₃⁺
δ = 9.45 (1H. broad α, removable with D₂O — CONH-)

| Analysis for C₂₄H₂₃N₃O₆S Cl₂ | | | | | | |
|---|---|---|---|---|---|---|
| | C | H | N | S | Cl | Cl⁻ |
| Required % | 52.18 | 4.17 | 7.61 | 5.80 | 6.43 | 6.43 |
| Found % | 49.31 | 4.05 | 7.05 | 5.78 | | 6.85 |
| | 49.16 | 4.07 | 7.08 | 5.61 | | 7.10 |
| | | | | | | 11.98 |
| | | | | | | 11.85 |

EXAMPLE 4 a. 4,5,6-Trimethoxy-Phthalide

Prepared by the action of formalin and concentrated hydrochloric acid on trimethyl gallic acid (3,4,5-trimethoxy-benzoic acid) by the method of King and King (J. Chem. Soc. 1942, 726–7).

b. 3-Bromo-4,5,6-Trimethoxy-Phthalide 4,5,6-Trimethoxyphthalide (11.4 gms; 0.05 mole), N-bromosuccinimide (8.9 gms; 0.05 mole) and azobisbutyronitrile) (0.1 gms) were refluxed gently in dry carbon tetrachloride (200 mls) for 2 hours. The solution was cooled, the succinimide filtered off and the solvent removed in vacuo, leaving a yellowish solid which fumed in the air.
Yield 14.7 gms; 97.1%
The solid was used immediately.

c. 4,5,6-Trimethoxyphthalide ester of 6[D(—)α-aminophenylacetamido] penicillanic acid, hydrochloride 6[D(—)N-(1-methoxycarbonylpropen-2-yl)-α-aminophenylacetamido] penicillanic acid, potassium salt (24.6 gms; 0.0486 mole) and 3-bromo-4,5,6-trimethoxyphthalide (14.7 gms; 0.0486 mole) were stirred in acetone (250 ml.) for 5 hours.

The mixture was filtered through Celite and evaporated to a foam in vacuo. The foam was dissolved in ethyl acetate (300 ml.) and washed with N/2 sodium bicarbonate solution (100 mls), water (100 mls.) and saturated brine (2 × 100 ml.). The solution was evaporated to a foam again and dissolved in acetone (100 ml.) with water (70 ml.). The pH at 1.9 on the pH meter by dropwise addition of 5N hydrochloric acid. The acetone was removed in vacuo and solid sodium chloride added to the residual aqueous layer and stirred for one-half hour.

The liquid was decanted from the precipitated solid and the latter dissolved in acetone, the solution dried over anhydrous magnesium sulphate and poured into dry stirring ether (4 lit.). The solid was filtered, washed with ether and dried to give the 4,5,6-trimethoxyphthalide ester of 6[D(—)α-aminophenylacetamido]penicillanic acid, hydrochloride.
Yield 20.6 gms. 69.5%.
Hydroxylamine Assay 115.9%.
I.R. Spectrum (KBr disc) shows the following inter alia strong bands:

1782 cm⁻¹ 1685 cm⁻¹ 1479 cm⁻¹ 1344 cm⁻¹
1333 cm⁻¹ 1309 cm⁻¹ 980 cm⁻¹

N.M.R. Spectrum ( (CD₃)₂SO) shows the following peaks:

δ = 1.47 (6H. m. Gem-dimethyls)
δ = 3.91 (3H. s. 4-methoxy-)
δ = 3.98 (6H. s. 5- and 6-methoxy)
δ = 4.51 (1H. d. J = 2 Hz. C₃ proton)
δ 5.16 (1H. broad s, sharpening on D₂₀ exchange

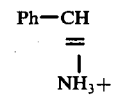

δ = 5.54 (2H. m. β-lactams)
δ = 7.45 (7H. m. phenyl aromatics phthalide 7-proton phthalide 3-proton)
δ = 9.05 (3H. broad s. removable with D₂O. —NH₃⁺
δ = 9.47 (1H. broad d. removable with D₂O. — CONH-).

| Analysis for C₂₇H₃₀N₃O₉SCl | | | | | |
|---|---|---|---|---|---|
| | C | H | N | S | Cl |
| Required % | 53.33 | 4.94 | 6.91 | 5.27 | 5.84 |
| Found % | 51.35 | 4.91 | 6.45 | 4.97 | 5.95 |
| | 51.41 | 4.90 | 6.54 | 4.52 | 5.14 |

EXAMPLE 5 a. 6-Bromo-Phthalide

Prepared by the action of bromine on phthalide in a melt of anhydrous aluminium chloride and urea as in the German Pat. No. 1,266,310.

b. 3,6-Dibromo-Phthalide

6-Bromophthalide (5.85 gms; 0.0275 mole), N-bromosuccinimide (4.89 gm; 0.0275 mole) and azobisbutyronitrile (0.1 gm) were gently refluxed in dry carbon tetrachloride (200 ml.) for 2 hours. On cooling, the succinimide was filtered off and the solvent removed in vacuo to give an oil, which was used immediately.

c. 6-Bromophthalide ester of 6[D(—)α-aminophenylacetamido]penicillanic acid, hydrochloride 6[D(—)N-(1-methoxycarbonylpropen-2-yl)-α-aminophenylacetamido] penicillanic acid potassium salt (13.9 gms; 0.0275 mole) and 3,6-Dibromophthalide (8 gm; 0.0275 mole) were stirred in dry acetone (200 ml.) overnight. The solution was filtered through Celite and evaporated in vacuo to a foam, which was dissolved in ethyl acetate (200 ml.). The solution was washed with N/2 sodium bicarbonate (100 ml.), water (100 ml.) and saturated brine (2 × 100 ml.). The solution was given evaporated to a foam in vacuo and dissolved in ethyl acetate (30 ml.) and poured into stirring 40°-60° petrol giving the 6-bromo phthalide ester of 6[D(—)N-(1-methoxycarbonylpropen-2-yl)-α-amino-phenylacetamido]penicillanic acid as a cream-coloured solid which was filtered, washed with petrol and dried.

Yield 10.6 gm. 58.3%

N.M.R. Spectrum ( (CD$_3$)$_2$SO) shows the following peaks:

δ = 1.50 (6H. m. Gem-dimethyls)
δ = 1.79 (3H. s. -OCH$_3$)
δ = 3.57

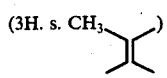
(3H. s. CH$_3$ )

δ = 4.52 (1H. s. C$_3$ proton)
δ = 4.55

(1H. s. H )

δ = 5.49 (2H. m. β-lactams)
δ = 5.65 (1H. broad s. α-proton)
δ = 7.39

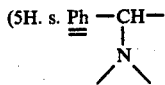
(5H. s. Ph —CH— )
          N

δ = 7.84 (4H. m. phthalide aromatics phthalide 3 proton)
δ = 9.0 − 9.5

(2H. m. removable with D$_2$O
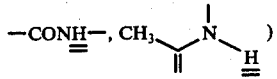
—CONH—, CH$_3$ N )
                  H

This ester was dissolved in acetone (120 ml.) and water (105 ml.) added. The pH was maintained at 1.8 by dropwise addition of 5N hydrochloric acid on the pH meter. The acetone was removed in vacuo and the aqueous solution extracted with ethyl acetate (20 ml.). The residual aqueous solution was salted with solid sodium chloride and the resulting oil separated, dissolved in acetone (50 ml.) and dried over anhydrous magnesium sulphate. The solution was poured into vigorously stirring dry ether (2.5 lit.) and the solid filtered, washed with ether, and dried to give the 6-bromophthalide ester of 6[D(—)α-aminophenylacetamido]penicillanic acid, hydrochloride.

Yield 4.2 gms; 43.7%

Hydroxylamine Assay 111.9%.

I.R. Spectrum (KBr disc) shows the following inter alia strong bands:

1780 cm$^{-1}$ 1683 cm$^{-1}$ 1291 cm$^{-1}$ 1079 cm$^{-1}$ 698 cm$^{-1}$

N.M.R. Spectrum ( (CD$_3$)$_2$SO) shows the following peaks:

δ = 1.44 (6H. m. Gem-dimethyls)
δ = 4.52 (1H. s. C$_3$-proton)

δ = 5.18 (1H. broad s, sharpening with D$_2$O. α-proton)
δ = 5.53 (2H. m. β-lactams)
δ = 7.75 (9H. m. phenyl- and phthalide aromatics and phthalide 3-proton).
δ = 9.7 − 9.5 (4H. removable with D$_2$O. -CONH-, -NH$_3^+$

| Analysis: Required % for C$_{24}$H$_{23}$N$_3$O$_6$S Cl Br | | | | | |
|---|---|---|---|---|---|
| C | H | N | S | Cl$^-$ | Br |
| 48.28 | 3.86 | 7.04 | 5.36 | 5.95 | 13.41 |
| 47.22 | 3.82 | 6.85 | 4.40 | 7.64 | 11.98 |
| 47.02 | 3.79 | 6.70 | 4.75 | 7.18 | 12.23 |

EXAMPLE 6 a. Preparation of 6-nitrophthalide

6-Nitrophthalide was prepared in 67.3% yield by the method of J. Tirouflet Bull. Soc. Sci. Bretagne. Spec. No. 26, 7-122 (1951) m.p. 142° -3° (from literature m.p. = 143°).

b. Preparation of 2-hydroxymethyl-5-nitro-N,N-dimethylbenzamide

To a stirred solution of 6-nitrophthalide (2 g.) in ethanol (120 ml.) at room temperature was added dimethylamine (in ethanol 33.3% solution: 50 ml.). After stirring for 5 hours the solvent was evaporated off. The resulting gum was dissolved in ethyl acetate. On addition of petrol 6° -80° a white solid crystallised out.

Yield = 1.77g = 70.8% m.p. = 106° -7°

I.R. Spectrum showed inter alia strong bands at: (nujol MuH) 745 cm$^{-1}$, 915 cm$^{-1}$, 1065 cm$^{-1}$, 1115 cm$^{-1}$, 1350 cm$^{-1}$, 1515 cm$^{-1}$, 1610 cm$^{-1}$ and 3300 cm$^{-1}$.

N.M.R. spectrum in CDCl$_3$ showed bands at:

δ = 2.92 and 3.17 (doublet = 6H = N,N-dimethyls)
δ = 4.03 (singlet = 1H = Ph—CH$_2$OH)
δ = 4.62 (singlet = 2H = Ph—CH$_2$OH)
δ = 7.58 − 8.28 (multiple bands = 3H = aromatic protons)

| ANALYSIS | | | |
|---|---|---|---|
| Required | C 53.60 | H 5.36 | N 12.48 |
| Found | C 53.50 | H 5.37 | N 12.50 |
| | 53.52 | 5.42 | 12.56 | c. Preparation of 2-carboxy-4-nitrobenzaldehyde

To a solution of 2-hydroxmethyl-5-nitro-N,N-dimethylbenzamide (17 g.) in glacial acetic acid (340 ml.) was added chromium trioxide (17 g.) in water (17 ml.) and glacial acetic acid (340-1). The reaction mixture was stirred at room temperature for 5 minutes, and then poured into ice-water (2 liters). The aqueous was extracted with chloroform (3 × 500 ml.). The chloroform extracts were combined and neutralised by washing with 10% sodium bicarbonate solution. The chloroform extracts were then washed thoroughly with water and dried over magnesium sulphate. The solution was then filtered and the solvent evaporated off to yield a gum.

Crude Yield = 15.0 g.

The gum was then refluxed in 3N hydrochloric acid (150 ml.) for 2½ hours. On cooling a white solid crystallised out. This was filtered off and dried.

Yield = 5.6 g. = 37.8% m.p. = 153°-4°

I.R. spectrum showed inter alia strong bands at: (nujol mull) 720 cm⁻¹, 900 cm⁻¹, 920 cm⁻¹, 1095 cm⁻¹, 1345 cm⁻¹, 1760 cm⁻¹ and 3325 cm⁻¹.

N.M.R. spectrum was consistent with the structures of the compound.

| Analysis | | | |
|---|---|---|---|
| Required | C 49.22 | H 2.56 | N 7.18 |
| | C 50.04 | H 2.78 | N 7.12 |
| | 49.78 | 2.73 | 7.20 | d. Preparation of 6-nitrophthalide ester of benzylpenicillin

To a suspension of benzylpenicillin sodium salt (7.12g: 0.02M) in dry methylene dichloride (50 ml.) at −5° C was added six drops of pyridine and ethyl chloroformate (2.17g; 1.91 ml; 0.02M). The reaction mixture was stirred at −5° C for one-half hour by which time the solution was almost clear.

A suspension of 2-carboxy-4-nitrobenzaldehyde (3.90g: 0.02M) in dry methylene dichloride (20 ml.) was added at 5° C. After one-half hour the reaction mixture was allowed to warm to room temperature, and then stirred for a further 4 hours.

The solution was then washed with 2% sodium bicarbonate solution (50 ml.) and water (3 × 50 ml.). The organic layer was dried over magnesium sulphate, filtered and the solvent evaporated off in vacuo.

The gum was dissolved in a small amount of ethyl acetate, filtered and dripped into excess petrol 40°-60°.

The resulting solid was filtered off and dried.

Yield = 1.6g = 15.7%

The bio-chromatogram showed two zones:

$R_f$ = 0.95 = 6-nitrophthalide ester of benzylpenicillin.

$R_f$ = 0.59 = benzylpenicillin.

The I.R. and N.M.R. spectra were consistent with a mixture of benzylpenicillin and the 6-nitrophthalide ester of benzylpenicillin.

EXAMPLE 7.

a. Peri — NAPHTHALDEHYDIC ACID.

Prepared by the action of 30% potassium hydroxide solution on acenaphthenequinone by the method of Fuson et. al. (J. Amer. Chem. Sec. 71, 1870.)

b. Peri — NAPHTHALIDE

Prepared by the action of formalin and potassium hydroxide on peri-naphthaldehydic acid by the method of Fuson et. al. (J. Amer. Chem. Soc. 71, 1870).

c. 3-Bromo- Peri- NAPHTHALIDE

Peri-naphthalide (1.7 gms, 9.23 m.mole), N-bromosuccinimide (1.64 gms; 9.23 m-mole) and azobisbutyronitrile (0.1 gm) were gently refluxed in dry carbon tetrachloride for 2 hours. The solution was cooled, the succinimide filtered off and the solvent removed in vacuo to leave the bromide which was used immediately.

Yield 1.3 gms 53.5%.

Peri-NAPHTHALIDE ESTER OF 6[D(−)α-aminophenylacetamido]penicillanic acid hydrochloride.

6[D(−)N- (1-methoxycarbonylpropen-2-yl)-α-aminophenylacetamido] penicillanic acid potassium salt (6.36 gms; 13.9 m.mole) and 3 bromo-peri-naphthalide (3.6 gms, 13.9 m.mole) were stirred in dry acetone overnight.

The mixture was filtered through Celite, evaporated in vacuo to a foam which was dissolved in ethyl acetate (100 ml) and washed with 1N sodium bicarbonate solution (50 ml), water (2 × 50 ml) and saturated brine solution (50 ml.). The solution was again evaporated in vacuo and dissolved in acetone (50 ml) with water (40 ml) and the pH maintained at 1.8 by addition of 5N hydrochloric acid dropwise.

The acetone was removed under reduced pressure and the resulting aqueous solution salted with solid sodium chloride, precipitating a gummy solid. The liquid was decanted off and the residue dissolved in a little acetone, dried over anhydrous magnesium sulphate and poured into an excess dry, stirring ether. The precipitated solid was filtered, washed with dry ether and dried, to give an impure sample of the 6[D(−)α-aminophenylacetamido] penicillanic acid peri-naphthalide ester, hydrochloride.

Yield 1.2 gms ca. 12%.

I.R. Spectrum (Nujol) shows the following inter alia strong bands:

1780 cm⁻¹ 1740 cm⁻¹ 1245 cm⁻¹ 1040 cm⁻¹ 792 cm⁻¹

N.M.R. spectrum ((CD₃)₂SO) shows the following peaks:

= 1.29 (6H.m. Gem-dimethyl)

= 4.40 (1H.d. - J = 2.5 Hz . C₃ proton)

= 5.13

(1H broad s, sharpening on D₂O exchange -

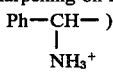

= 5.45 (2H. m. β-lactams)

= 7.51

(5H. s. Ph—CH— )

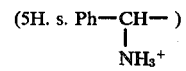

= 7.3 −8.8 (7H. m. naphthalide aromatics and naphthalide C₃ proton).

= 8.8 − 10 (3H. diffuse peak removable on D₂O exchange——NH₃⁺)

| Analysis for C₂₈H₂₆N₃O₆SCl | | | | | |
|---|---|---|---|---|---|
| | C | H | N | S | Cl |
| Required % | 59.21 | 4.58 | 7.40 | 5.64 | 6.26 |
| Found | 59.02 | 5.30 | 6.11 | 4.34 | 5.09 |
| | 59.70 | 5.45 | 6.09 | 4.96 | 5.36 |

EXAMPLE 8.

a. CROTONOLACTONE.

Prepared by the method of C.C. Price et al., (Org. Syn. 45 22 1965) in 33% yield.

b. 3-BROMO CROTONOLACTONE

Crotonolactone (0.84 g. 0.01 m) was added to a stirred suspension of N-bromo succinimide (.78 g, 0.01 m) in dry carbon tetrachloride (50 mls) The mixture was heated to reflux and a catalytic amount of aza-isobutyronitrile was added. The reaction was continued for 1 hour during which time the mixture turned red/brown. The reaction mixture was cooled, filtered and washed successively with sodium bicarbonate solution (2% w.v,) and water and then dried (Mq SO₄). The solvent was evaporated in vacuo and the product isolated as a syrup.

Yield 0.8 g (49%) n.m.r. (CD Cl₃)
6.23 (1.H. q. α proton)
6.96 (1.H. d. γ proton)
7.62 (1.H. q. β proton) + impurity peaks at higher yield.

3-CROTONOLACTONYL EST R OF 6
[D(—)α-aminophenylacetamido]penicillanic acid, hydrochloride.

To the stirred dispersion of the potassium salt of 6[D(—)N-(1-methoxycarbonylpropen-2-yl)-α-aminophenylacetamido]. penicillanic acid (10.1g, 0.02 m) in dry acetone, a freshly prepared crude preparation of γ - bromo - crotonolactone was added in one portion. The mixture was then stirred at ambient temperature for a total of 12 hours.

The reaction mixture was filtered and the solvent evaporated in vacuo to give a brown oil. The oily residue was dissolved in ethyl acetate (250 ml) and a brown precipitate was obtained on standing; this was removed by filtration and discarded. The filtrate was then washed with water (3 × 100 mls) and dried (MgSO₄).

The solvent was evaporated in vacuo and the resultant oil was dissolved in acetone (200 mls). Water (150 mls) was added to the solution and the whole mixture was stirred vigorously whilst the pH was adjusted to 2.5 with dilute hydrochloric acid over a period of 20 minutes. The acetone was then removed by evaporation in vacuo and the aqueous phase was extracted with ethyl acetate (150 mls) and separated. Petroleum ether (40°-60° C; 70 mls) was added to the ethyl acetate phase and the solution was again extracted with water pH 3. The aqueous phase was then combined, saturated with sodium chloride and stirred vigorously. A brown oil separated which was collected, dissolved in isopropanol (50 mls) and filtered. The filtrate was then dripped slowly into an excess of anhydrous ether (750 mls) and yielded a white flocculent solid. The precipitate was filtered, washed extensively with petroleum ether (40°-60° C) and ether and then dried in vacuo.

Yield 2.8g (30% based on penicillin).
$C_{20}H_{22}O_6N_3$ S Cl required: C51.34; H 4.71; N 8.98 S 6.84; Cl 7.59
found : C49.09; H 4.77; N.8.49;S 6.20; Cl 7.28 n.m.r. ( $(CD_3)_2 SO/D_2O$).

δ 7.7 (1.H.m β proton crotonolactone)
δ 7.5 (5.H.m aromatics)
δ 7.11 (1.H.d γ-proton crotonolactone)
δ 6.57 (1.H.q. α-proton crotonolactone )
δ 5.52 (2.H.q. β-lactam )
δ 5.14 (1.H.s. α-proton )
δ 4.50 (1.H.s. C-3 proton )
δ 1.42 (6.H.d. Gem-dimethyls. )
i.r. (K Br) strong bands at 1775 cm⁻¹ (broad), 1680 cm⁻¹, 1085 cm⁻¹, 1000 cm⁻¹.

Biochromatogram: $R_f$ 0.80 (ester) together with the parent ampicillin $R_f$ 0.35 resulting from hydrolysis or the chromatographic treatment; streaking between the two zones was also apparent.

EXAMPLE 9.

a. Preparation of 3-thiophthalide.

O-cyanobenzylbromide was converted to o-cyanobenzylthiocyanate using potassium thiocyanate in ethanol. This went in 96% yield by the method of A. W. Day and S. Gabriel, Berichte 1890 23 2478-89. o-cyanobenzylthiocyanate was converted to o-cyanobenzylmercaptan using concentrated sulphuric acid in 93% yield, using the method of M.Renson and R. Collienne.-Bull.Soc.Chim.Belges. 73. (5-6) 491-506 (1964). O-Cyanobenzylmercaptan was converted into 2-thiophthalide by the action of boiling water by the method of M.Renson etc. in 45% yield.

b. Preparation of 3-brom-2-thiophthalide.

To a solution of 2-thiophthalide (5.0 g: o.033M) in dry carbon tetrachloride (100 ml) was added N-bromosuccinimide (5.72 g. 0.033M) and a catalytic amount of αα'-aziosobutyronitrile. The reaction mixture was refluxed gently for 1 hour, and then cooled. The solution was refluxed gently for 1 hour, and then cooled. The solution was filtered and the solvent evaporated off. The product was recrystallised from cyclohexane.

Yield = 4.5 g. 9 (70.11%).
I.R. spectrum showed inter alia strong bands at:
(nujol mull) 690 cm⁻¹, 770 cm⁻¹, 905 cm⁻¹, 1240 cm⁻¹, and 1700 cm⁻¹
N.M.R. spectrum showed bands at:
δ = 6.75 (singlet = 1H = phthalide CH)
δ = 7.42 - 7.90 (multiplet = 4H = phthalide aromatics)

c. Preparation of 2-thiophthalide ester of 6[D(—)α-aminophenylacetamido] penicillanic acid, hydrochloride.

A suspension of potassium salt of 6[D(—)N-(N-(1-methoxycarbonylpropen-2-yl) α-aminophenylacetamido]penicillanic acid (10.07g. 0.02M) was stirred at 0°C in dry acetone (100 ml.). To this was added 3-bromo-2-thiophthalide (4.58g. 0,02M) in dry acetone (20ml.). The reaction mixture was allowed to warm to room temperature and stirred for a further 5 hours. The reaction mixture was then filtered and the solvent allowed to evaporate off in vaccuo. The resulting gum was dissolved in ethyl acetate (100ml.) and vigorously stirred. Water (100ml) was added and the pH adjusted to 2.0 with 5N hydrochloric acid. The organic layer was retained and washed with water (50ml) and brine. The ethyl acetate solution was dried over magnesium sulphate, filtered and evaporated in vaccuo. The resulting gum was triturated with petroleum ether 40°-60° and the solid obtained filtered off and dried.

Yield: 3.4g. (32.1%).
i.r. spectrum showed strong bands at 780 cm⁻¹ 915 cm⁻¹ 1175 cm⁻¹ 1590 cm⁻¹ 1750 cm⁻¹ 1780 cm⁻¹.
n.m..r. $(CD_3)_2SO/D_2O$: δ=1.50(m. gem dimethyls) 4,55(d. C₃ proton)
5.50(m. β-lactam proton) 7.36 (s. phenyls) 7,48 (d. phthalide CH) 7.80 (broad band. phthalide aromatics.).

EXAMPLE 10

PREPARATION OF 5,6-DIMETHOXYPHTHALIDE BENZYLPENICILLIN.

Potassium-benzylpenicillin (2.73 g., 0.00734 mole) was stirred in dry D.M.E. (100 ml.) with 3-bromo-5,6-dimethoxyphthalide (2.0 g., 0.00734 mole) for 12 hours. The mixture was poured into iced water (2 lits) with vigorous stirring and the solid filtered, dried and crystallised from isopropanol.

Yield: 1.6 g. 41.5% M.P.: 98–100° C $NH_2OH$: 127.7%

| Analysis: | C | H | O | S | |
|---|---|---|---|---|---|
| Required: | 59.32 | 4.94 | 5.32 | 24.33 | 6.08 |
| Found: | 58.25 | 4.94 | 5.04 | — | 5.99 |
|  | 58.37 | 4.98 | 5.03 | — | 5.97 |

I.R. spectrum (Nujol) contains the following inter alia strong bands:
1770 $cm^{-1}$ 1338 $cm^{-1}$ 1285 $cm^{-1}$ 985 $cm^{-1}$ 970 $cm^{-1}$ N.M.R. spectrum $(CD_3)_2SO$ shows the following peaks:

$\delta$ = 1.52 (6H.m.) Gem-dimethyls
$\delta$ = 3.54 (2H.s.) Benzyl — $CH_2$ —
$\delta$ = 3.90 (6H.s.) Methoxy-groups
$\delta$ = 4.50 (1H.s.) $C_3$ proton
$\delta$ = 5.50 H.m.) (2- lactams
$\delta$ = 7.25 (5H.s.) Benzyl aromatics
$\delta$ = 7.37 (2H.m.) Phthalide aromatics
$\delta$ = 7.43 (1H.s.) Phthalide 3-proton
$\delta$ = 8.6 – 8.8 (1H.m.) -CON$\underline{H}$-

EXAMPLE 11

3-CROTONO LACTONYL ESTER OF BENZYLPENICILLIN

The sodium salt of benzylpenicillin (1.6g., 0.0044 m) was dispersed in dry dimethylformamide (40 mls.) and the mixture was chilled to 0° C. To the stirred solution, a crude preparation of 3-bromo-crotonolactone (0.7g., 0.0043m assuming absolute purity) was added in one portion and the reaction was continued for 30 minutes at 0° C and a further 2 hours at room temperature.

The reaction mixture was poured into ice water (400 mls) and the resulting brown coloured emulsion obtained was then extracted with ethyl acetate. The organic phase was then washed with diluted sodium bicarbonate solution (2% w/v) and water and finally dried ($MgSO_4$). The solution was filtered and the solvent evaporated in vacuo to yield a darkly coloured oil. The oil was triturated with petroleum ether (40°–60° C) and then treated with a mixture of isopropanol, isopropyl ether to yield a brown amorphous solid (Yield 240mg. 13%)

$C_{20}H_{20}O_6N_2S$ requires C 57.75; H 4.8; N 6.73 found C 57.69; H 5.20; N 6.14

N.M.R. $(CDCl_3)$:

$\delta$7.53–7.18 (6H. m. aromatic protons + $\beta$- proton crotonolactone)
$\delta$7.04 (1 H. d, $\gamma$-proton crotonolactone)
$\delta$6.36 (1H. m.$\alpha$-proton crotonolactone)
$\delta$6.20 (1 H d NHCO)
$\delta$5.83-5.38 (2H.m. $\beta$-lactams)
$\delta$4.40 (1H s C-3 proton)
$\delta$3.63 (2H s Ph $CH_2$)
$\delta$ 1.48 (6H d gem-dimethyls)

I.R. (K Br.) strong bands at $1775^{-1}$ $16.65^{-1}$ $1083^{-1}$ $1000^{-1}$

EXAMPLE 12

6-METHOXY-PHTHALIDE BENZYLPENICILLIN

Benzylpenicillin, potassium salt (3.59gms; 0.00966 M) and 3-bromo-6-methoxyphthalide (2.35gm; 0.00966 M) were stirred over-night in dry dimethylformamide.

The mixture was poured into water (1 lit.) and stirred for ½-hour. Solid sodium chloride was then added to the resulting emulsion and the solid filtered, washed well with water and dried.

Yield gms 33.8%
Hydroxylamine Assay 110.5%

I.R. (KBr disc) showed the following inter alia strong bands:
1780 $cm^{-1}$ 1670 $cm^{-1}$ 1496 $cm^{-1}$ 1321 $cm^{-1}$
1284 $cm^{-1}$ 1246 $cm^{-1}$ 1049 $cm^{-1}$ 976 $cm^{-1}$ N.M.R. $(CD_3)_2SO$
$\delta$ = 1.59 (6H - m gem-dimethyls)
$\delta$ = 3.54 (2H - s benzyl - $CH_2$-)
$\delta$ = 3.90 (3H - s methoxy-protons)
$\delta$ = 4.51 (1H - s $C_3$ - proton)
$\delta$ = 5.50 (2H - m $\beta$- lactams)
$\delta$ = 7.27 (5H - s benzyl aromatics)
$\delta$ = 7.47 (3H m phthalide aromatics)
$\delta$ = 7.52 (1H - s phthalide $C_3$ proton)
$\delta$ = 8.4 - 9.1 (1H m. –CON$\underline{H}$ –)

EXAMPLE 13

3-Phenylphthalide Phenylacetamidopenicillanate.

Ethyl chloroformate (4.8ml. 0.05M) and pyridine (10 drops) was added to a stirred solution of sodium phenylacetamidopenicillanate (18.5g. 0.05M) in methylene dichloride (250ml) at −10° C. After stirring for ½ hr an almost clear solution was obtained to which a solution of 2-benzoylbenzoic acid (11.3g. 0.05M) in methylene dichloride (100ml) was added and the mixture stirred at ambient temperature for 3–4 hours. A fine white solid which precipitated during the course of the reaction was filtered off and the chloroform removed in vacuo to leave a pale yellow foam which was dissolved in ethyl acetate (500ml). Insoluble material was filtered off and the clear yellow filtrate was washed twice with 200ml portions of 1N sodium bicarbonate and twice with 200ml portions of a saturated brine solution.

After drying over anhydrous magnesium sulphate, the ethyl acetate layer was filtered and concentrated in vacuo to give a yellow foam, which was dissolved in diethyl ether (100ml) and added dropwise with stirring to a solution of petroleum ether 40°-60° (about 500ml). The ester precipitated immediately as a pale yellow amorphous powder (6.8g. 25.3%)

I.R. (KBr disc): Strong bands at 1780 $cm^{-1}$ 1650 $cm^{-1}$ 1510 $cm^{-1}$ 1290 $cm^{-1}$ 1210 $cm^{-1}$ 1005 $cm^{-1}$ 942 $cm^{-1}$ 700 $cm^{-1}$.

N.M.R. $(CD_3)_2SO$: =7.9–7.2 (14H.m. 2 broad bands and 1 sharp singlet) 5.5 (2H.m. $\beta$-lactam protons) 3.58 (2H.s. Ph.$CH_2$.CO—) 1.55 (6H.d. gem dimethyls).

Hydroxylamine assay=112.7%.

EXAMPLE 14.

3,3 Methyl Valerolactonyl ester of phenoxymethylpenicillin.

The potassium salt of phenoxymethylpenicillin (5.8g. 0.015m) was dispersed in dry dimethylformamide (50 mls) and the mixture was chilled to 0° C. A constant stream of nitrogen was bubbled through the mixture and freshly prepared crude 3-chloro-3-methyl-butyrolactone (2.1 gms, 0.015m) was added to one portion together with a catalytic quantity of sodium iodide. The reaction was maintained at 0° C for 15 minutes, allowed to warm to room temperature and then continued for a further 30 minutes. The whole mixture was then poured into ice water and the white precipitate obtained was filtered, washed with water and dried in vacuo to yield a brown solid (3.2gms. 48%) Biochromatographic evidence showed the product was composed of the required ester (Rf 0.95) together with a small quantity of the parent penicillin (Rf 0.65).

The product was further purified by washing with sodium bicarbonate solution (1N) and finally recrystallising from warm isopropanol $C_{21}H_{24}O_7N_2S$ requires C 56.25; H 5.58; N 6.25; S 7.14. found C 56.17; H 5.45; N 6.00; S 7.39.

n.m.r. (CDCl$_3$)

6.7–7.6 (6H.m. NHCO + phenyl aromatics)
5.5–5.9 (2H.m. β-lactams)
4.58 (2H.s. PhO.CH$_2$)
4.43 (1H.s. C-3 proton)
2.0–2.95 (4H.m. butyrolactone methylene protons)
1.85 (3H.d. CH$_3$-C-O
1.58 (6H.s. gem-dimethyls)

i.r. (KBr) Strong bands of 1780 cm$^{-1}$, 1750 cm$^{-1}$, 1685 cm$^{-1}$, 1078 cm$^{-1}$.

EXAMPLE 15.

3.3-Methyl phthalide ester of benzylpenicillin. Method.

As in Example 14. Crude yield (containing benzylpenicillin as indicated by biochromatogram Rf 0.60) 65%.

Following further purification by chromatography on silica gel using ethyl acetate petroleum ether (60°–80°) (4:1) as elutant and treatment with sodium bicarbonate solution, a product was obtained as an amorphous white solid from ether/petroleum ether (40°–60° C).

$C_{25}H_{24}O_6N_2S$ requires C 62.50; N 5.00; N 5.83 found C 61.89; H 5.23; N 6.05 n.m.r. (CDCl$_3$)

8.1–7.5 (4H.m. phthalide aromatics)
7.3 (5H.s. phenyl aromatics)
6.35–5.9 (I.H.m. broad NH CO)
5.80–5.30 (2.H.m. β-lactams)
4.3 (I.H.m. C-3)
3.63 (2H.s. PhCH$_2$)
2.00 (3H.d. O.C.-CH$_3$)
1.45 (6H.s. gem dimethyls).

i.r. (KBr) strong bands at 1780 cm$^{-1}$, 1665 cm$^{-1}$, 1285 cm$^{-1}$, 925 cm$^{-1}$.

EXAMPLE 16.

3-Methyl phalide ester of 6-[D(−)α-aminophenylacetamido]penicillanic acid hydrochloride. Method.

The 3,3 methyl phthalide ester of phenoxymethylpenicillin (Example 14) was cleaved by known methods using PCl$_5$ followed by treatment with methanol and hydrolysis to give the corresponding 6APA ester. The product was isolated as the para-toluene sulphonate salt.

The 6APA ester was then acylated using D(−)N-(1-methoxycarbonylpropen-2-yl)-α-aminophenylacetate via the ethoxy formic mixed anhydride and isolated as the 6[D(−)α-aminophenylacetamido]penicillanic acid hydrochloride salt following treatment with dilute hydrochloric acid.

i.r. (KBr) strong bands at 1780 cm$^{-1}$, 1675 cm$^{-1}$, 1495 cm$^{-1}$.

EXAMPLE 17.

3-Methyl Phthalide Ester of Phenoxymethylpenicillin via the mixed anhydride route.

Method.

The potassium salt of phenoxymethylpenicillin (11.64g, 0.03 m) was dispersed in dry methylene dichloride (200 mls) and the mixture chilled to −5° C. To the stirred suspension, ethyl chloroformate (3.24g, 0.03m) was added dropwise together with a catalytic quantity of pyridene. The mixture was stirred at −5° C for 30 minutes.

o-Acetyl benzoic acid (4.92gm 0.03m) was dissolved in dry ethyl acetate (150 mls) and the solution was then added to the reaction mixture. The reaction was continued at ambient temperature for 18 hours.

The solvent was evaporated in vacuo to yield a mobile straw coloured syrup. The syrup was dissolved in ethyl acetate (250 mls) and washed successively with dilute bicarbonate solution (100 mls, 0.25N) and water (100 mls) and then dried over anhydrous magnesium sulphate. The drying agent was filtered off and the solvent removed in vacuo to yield a foam.

T.l.c. and n.m.r. evidence showed the product to be the required ester contaminated with some small degree with unknown materials. The ester was therefore further purified by column chromatography using silica gel and ethyl acetate, petroleum ether (60–80° C) (4:1 ratio) as elutant. The appropriate eluted fractions were combined and the solvent evaporated in vacuo to yield a gum. An amorphous solid was obtained by firstly triturating the gum with anhydrous ether and then with an acetone, ether mixture and pouring the respective solutions into petroleum ether (40–60). Yield 4.7g (31%).

$C_{25}H_{24}O_7N_2S$ requires C 60.48; H 4.84; N 5.64 found C 60.06; H 4.90; N 5.70.

n.m.r. (CDCl$_3$)

δ 8.0–7.5 (4H.m. phthalide aromatics)
δ 7.5–6.75 (6H.m. NHCO + phenyl aromatics)
δ 5.85–5.4 (2H.m. β-lactams).
δ 4.55 (2H.s. OCH$_2$)
δ 4.39 (IH.d. C-3 proton)
δ 2.00 (3.H.d. CO.OC-CH$_3$)
δ 1.65-1.35 (6.H.m. gem dimethyls).

i.r. (KBr) strong bands at 1780 cm$^{-1}$, 1685 cm$^{-1}$, 1285 cm$^{-1}$ and 925 cm$^{-1}$.

Biochromatogram: Rf 0.95.

EXAMPLE 18.

3-Methyl phthalide ester of phenoxymethylpenicillin via the corresponding ester of benzene sulphonic acid.

Method.

o-Acetyl benzoic acid (4.92g, 0.03m) was dispersed in dry ethyl acetate (100 mls) and chilled to 0° C. Dry pyridene (2.37g. 0.03m) was then added to the stirred suspension followed by the dropwise addition of benzene sulphonyl chloride (5.31g., 0.03m). The mixture was allowed to stand for a protracted period at 4° C.

The reaction contents were warmed to ambient temperature and the potassium salt of phenoxymethylpenicillin (11.64g 0.03m) was added with stirring. The reaction was then allowed to continue for a further 18 hours.

The mixture was filtered to yield a yellow filtrate and a solid residue; the latter was discarded. The filtrate was washed with dilute sodium bicarbonate solution (3 × 100 mls, 2% w/v), water (2 × 100 mls) and brine and finally dried over anhydrous sodium sulphate. The solution was then filtered and the solvent evaporated in vacuo to yield a yellow syrup. The syrup was dissolved in the minimal quantity of acetone, diluted with ether and the solution was then poured into excess petroleum ether (40°-60° C) affording an amorphous yellow solid. The product was filtered, washed with petroleum ether and dried in vacuo (Yield: 2.5g, 17%). The ester was characterised by n.m.r. and i.r. and displayed spectra identical to that of an authentic sample.

EXAMPLE 19.

a. Preparation of o-acetyl phenyl acetic acid. Method.

3-Methyl indene was prepared by dehydrating the carbinol, with acid, formed from the Grignard reaction of 1-indanone with methyl magnesium iodide, o-acetylphenyl acetic acid was prepared from 3-methyl indene by a dichromate oxidation in 58% yield.

b. Preparation of the 1-methyl-isochroman-3-one ester of phenoxymethylpenicillin.

Method.

To a stirred suspension of phenoxymethylpenicillin potassium salt (7.76g. 0.02M) in methylene dichloride (100-1) at −5° C was added pyridine (6 drops) and ethyl chloroformate (1.91 ml: 0.02M) The mixture was stirred at −5° for ½ hour. A suspension of o-acetyl phenyl acetic acid (3.56g: 0.02M) in dry methylene dichloride (50 ml) was added. The reaction mixture was stirred at −5° for ½ hour and then allowed to warm to room temperature and stirred for a further 4 hours. The now almost clear solution was water washed, dried over magnesium sulphate, filtered and the solvent evaporated in vacuo to give a solid foam.

Yield: 2.0g = 15.6%

The biochromatogram showed a zone $R_f = 0.94$ which was the ester, it also showed signs of hydrolysis in the form of streaking to a zone or $R_f = 0.63$ which was the parent penicillin.

I.R. spectrum (nujol mull) showed into alia strong bands at: 705 cm$^{-1}$, 765 cm$^{-1}$, 1215 cm$^{-1}$, 1495 cm$^{-1}$, 1735 cm$^{-1}$, and 1780 cm$^{-1}$.

NMR spectrum $(CD_3)_2SO + D_2O$ showed bands at:

$\delta = 1.52$ (doublet = gem di methyls)
$\delta = 2.10$ (singlet = 1-methyl group)
$\delta = 3.85$ (singlet = Ph—OCH$_2$CONH—)
$\delta = 4.67$ (broad singlet = CH$_2$ of lactose ring)
$\delta = 5.00$ (broad singlet — C$_3$ proton)
$\delta = 5.58$ (multiplet = β-lactam protons)
$\delta = 6.80$–7.50 (broad multiplet = aromatic protons.)

EXAMPLE 20.

Peri-naphthalide Ester of Phenoxy-methyl penicillin.

Phenoxymethyl penicillin, potassium salt (15.52 gms; 0.04 mole) in dry methylene dichloride (200 mls) was cooled to −5° C and treated with ethyl chloroformate (4.34 gm; 3.82 ml; 0.04 mole) and pyridine (0.4 ml) and stirring continued for 1 hour at −5° C.

Peri-naphthalaldehydic acid (200 ml) was added to the mixed anhydride solution and the mixture stirred for 4 hours at room temperature.

The mixture was filtered through Celite washed with N/2 sodium bicarbonate solution (100 ml), water (100 ml) and saturated brine (100 ml), and dried over anhydrous magnesium sulphate. The solution was evaporated in vacuo to low volume and poured into 40°-60° petrol (3 lit.) with vigorous stirring. The solid was filtered, washed with petrol and dried.

Yield 3.1 gms 14.6%

I.R. Spectrum (KBr disc) shows the following inter alia strong bands:

1780 cm$^{-1}$, 1740 cm$^{-1}$, 1513 cm$^{-1}$, 1256 cm$^{-1}$, 1241 cm$^{-1}$, 1074 cm$^{-1}$, 782 cm$^{-1}$, 757 cm$^{-1}$.

N.M.R. Spectrum $((CD_3)_2SO)$ shows the following peaks:

$\delta = 1.50$ (6H.m. Gem-dimethyls)
$\delta = 4.55$ (IH.d J=2,5Hz, C$_2$ proton)
$\delta = 4.68$ (2H.s. PhOC$\underline{H}_2$—)
$\delta = 5.59$ (2H.m. β-lactams)
$\delta = 5.8$–8.7 (13H.m. Naphthalide aromatics, Phenoxy-aromatics Naphthalide C$_3$ protons. CO—N$\underline{H}$—(removable with D$_{20}$)

| Analysis for C$_{28}$H$_{24}$N$_2$O$_7$S | | | | |
|---|---|---|---|---|
| | C | H | N | S |
| Required % | 63.16 | 4.51 | 5.26 | 6.0 |
| Found % | 62.57 | 4.57 | 4.30 | 4.36 |
| | 61.76 | 5.02 | 4.57 | 4.24 |

EXAMPLE 21.

3-Phenyl phthalide ester of Phenoxymethylpenicillin.

The potassium salt of phenoxymethylpenicillin (7.76g. 0.02m) was dispersed in dry dimethyl formamide (75 mls) at ambient temperature. The acid chloride of o-benzoyl benzoic acid (4.9g, 0.02m) was added to the stirred suspension and the reaction was continued at room temperature for 4 hours.

The reaction mixture was then poured into ice water (600 mls) and the brown precipitate which was obtained was extracted into chloroform (4 × 400 mls). The chloroform solution was washed successively with water (3 × 200 mls), dilute sodium bicarbonate solution (2 × 200 mls, 2% w/v), water (2 × 200 mls) and finally brine. The solution was then dried (Na$_2$SO$_4$), filtered and diluted with petroleum ether (40°-60° C). A small quantity of a flocculent precipitate was obtained which was filtered and discarded. The filtrate was dripped slowly into an excess of petroleum ether (40°-60° C) to yield a brown amorphous solid. Yield 2.4g (21%).

Biochromatographic evidence showed the product to be the required ester (Rf 0.95). T.l.c. data showed the product to contain a small quantity of the present acid chloride intermediate; this latter result was also reflected in the n.m.r. data.

n.m.r. $\delta$ 815–6.75 (14H m. phthalide aromatics $((CD_3)_2SO)$. 10 phenyl aromatics + 3H due to impurity — presumably acid chloride intermediate).

$\delta$ 5.85–5.4 (2.H. m. β lactams)
$\delta$ 4.8–4.55 (3.H. m. C-3 proton plus —OC$\underline{H}_2$)
$\delta$ 1.53 (6H. d. gem. dimethyls).

EXAMPLE 22.

Phthalide Ester of Azidocillin.

To a suspension of the medium salt of azidocillin (6.64g) in 30 mls of dimethylformamide was added at room temperature. 3.10g. of 3-bromonaphthalide as a solution in 10 ml. of dimethylformamide. The suspension was stirred over night at room temperature at the end of which a clear solution remained. This was poured into iced water, acidified and extracted with ethyl acetate. The organic layer was washed with sodium bicarbonate, brine, dried over Mg $SO_4$ and stripped to leave a yellow gum. 7.3 gm, 96% yield. An analytically pure sample could be obtained as a white sticky gum by chromatography as silica gel, and identified as the phthalide ester of [D]α-azidobenzyl penicillin on the basis of the following properties.

Hydroxylamine assay 105.1%
I.R. (neat) ν max = 3280 (NH) cm $^{-1}$
= 2120 ($N_3$) cm$^{-1}$
= 1775 (β-CO) cm$^{-1}$
= 1725 (ester) cm$^{-1}$
= 1680 (amide) cm$^{-1}$
= 1595 (aromatic) cm$^{-1}$
NMR ($CDCl_3$) δ = 1.61 (6H, gem dimethyl)
= 4.52 (2 singlets, $C_3$—H)
= 5.11 (singlet, $C_2$—H)
= 5.56 (split quartet, $C_6$, $C_5$ protons) J = 4 cps.
= 2.1-2.6 (9 aromatic protons, phthalide $C_3$—H)

(I)

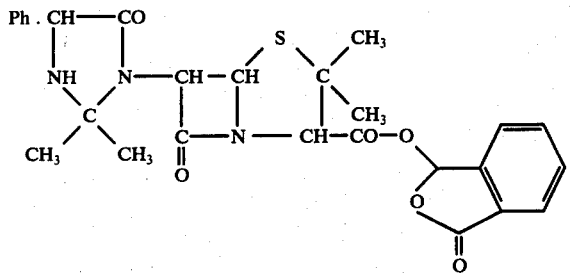

EXAMPLE 23.

Phthalide ester of hetacillin (I).

METHOD.

Hetacillin (2g, 0.0051 m) together with triethylamine (0.72 mls, 0.0051 m) were dispersed in dry dimethylformamide (25 mls) and the suspension was chilled to 0° C. To the stirred mixture, 3-bromophthalide (1.09g, 0.0051 m) was added in one portion. The cooling bath was then removed and the reaction allowed to warm to ambient temperature. The reaction was continued for 90 minutes.

The resulting mixture was then poured in ice water; the white precipitate obtained was filtered, washed extensively with water and finally freeze dried to yield a white amorphous solid.

Yield 1.33g. 51%.
n.m.r. (($CD_3)_2SO$)
δ 7.88 (4.H.m. phthalide aromatics)
δ 7.62 (I.H.d. CO.O CH O)
δ 7.6–7.15 (5.H.m. phenyl aromatics)
δ 5.50 (IH d. J 4Hz C—6 proton)
δ 5.19 (IH d J 4Hz C—5 proton)
δ 4.65 (IH.s. PhCH NH)
δ 4.58 (IH.S. C—3 proton)
δ 1.75–1.15 and 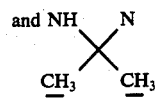

i.r. (Nujol strong bands at 1785 cm$^{-1}$, 1700 cm$^{-1}$ and 980 cm$^{-1}$.

Biochromatogram: Rf 0.85 (ester) together with trace amount of the parent penicillin Rf 0.33.

EXAMPLE 24.

Phthalide ester of D,L β-amino-β-cyclohex-3-enyl ethyl penicillin.

A solution of cyclohex-3 enecarboxaldehyde (55g., 0.5m), malonic acid (52g., 0.5m) and ammonium acetate (77g., 1.0m) in 95% ethanol in water (150 ml.) was refluxed between 70°–80° C for 24 hours. On cooling, a white solid precipitated out of the reaction mixture. This was collected, washed with acetone and disiccated over phosphorous pentoxide for 24 hours. The filtrate was reduced in volume and diluted with acetone resulting in a further batch of product being isolated.

Both crops were identified as D,L β-amino β-cyclohex-3 enyl propionic acid (m.p. 208°–210° C, 60g., 70% yield); Found: C 63.66 H 9.05 N 8.15% $C_9H_{15}N$ $O_2$ requires C 63.9 H 8.77 N 8.27%; ν (mull) 1630 C=C, 1550 cm $^{-1}$ $CO_2^-$ δ($D_2O+DCl$) 5.8 (2H,S (3,4 vinyl protons) 3.6 (H,M,β proton) 2.8 (2H,S and q, α protons) 2.0 (7H,m, cyclohexyl protons); zero optical rotation.

The sodium salt of D,L β-amino β-cyclohexzenyl propionate was prepared in situ by addition of the β-amino acid (16.9g., 0.1m) to a solution of sodium (2.3g 0.1m) in absolute ethanol (150 ml). Methyl acetoacetate (11.6g., 0.1m) was added and the reaction mixture heated under reflux for 3 hours. The reaction mixture was filtered while still hot and, in cooling, white needles of the enamine derivative were obtained. These were collected, washed with ether and desiccated for at least 48 hours over anhydrous calcium chloride in a vacuum oven at 70° C. This gave sodium D,L β-amino (N-metoxy-carbonylpropen-2-yl)β-cyclohex-3-enyl propionate in quantitative yield (m.p. 186°–1° C) Found: C 58.1 H 6.91 N 4.85% $C_{14}H_{20}N$ $O_4$No requires C 57.85 H 7.0 N 4.77; ν(KBr) $CO_2Ml$ 1640, $CO_2$— 1580 cm$^{-1}$; δ ($CD_3)_2SO$ 9.0 (H,d,NH), 5.78 (2H, S, Chd 3,4 vinyl protons), 4.25 (H, S, enamine vinyl protons), 3.6 (H,m,β protons) 3.5 (3 H,S, methoxy protons), 2.0–1.7 (10H,m, enamine methyl and cyclohexyl protons); zero optical rotation. Ethyl chloroformate (0.74g 5 mM) and N-methyl morpholine (1 drop) were added to a suspension of sodium β-amino (N-methoxycarbonylpropen-2-yl) β-cyclohex-3-enyl propionate (1.48g, 5 mM) in anhydrous acetone (40 ml) at −20° C. The reaction mixture was stirred for 20 minutes at −5° to −10° C. yielding the mixed anhydride derivative.

p-Toluenesulphonate salt of phthalide 6-amino penicillinate (2.6g, 5 mM) in anhydrous acetone (20 ml) was neutralised with triethylamine (0.7 ml) and cooled to −20° C. The mixed anhydride solution at −30° C was added and the resultant cloudy mixture stirred for an hour, its temperature being allowed to reach 20° C.

The acetone was removed in vacuo and the residue yellow gum was dissolved in 50% mixture of ethyl acetate and water (100 ml). This was adjusted to pH 1.5 with 5N hydrochloric acid and maintained at this pH for 30 minutes. The phases were separated and the yellow ethyl acetate layer washed with water (3 × 25 ml), saturated brine (50 ml) and filtered through a silicone treated filter paper. A light yellow gum was obtained on evaporation of the solvent in vacuo. This on trituration with anhydrous ether gave a light yellow solid — the phthalide ester of D,L β-amino β-cyclohex-3-enyl ethyl penicillin in 70% yield m.p. 120 dec ν (KBr) β lactam, ester C=O 1780, 2° amido 1650, $CO_2$ −1600 cm$^{-1}$ δ $(CD_3)_2CO$ 8.0–7.3 (m, phenylprotons) 5.65 (m β-lactam, vinyl protons) 2.0–1.0 (m, cyclohexyl and gem dimethyl protons). Biochromatogram (n Butanol/ethanol) of the penicillin showed a single zone Rf. 0.95 and its purity by hydoxylamine assay 74.2%.

EXAMPLE 25.

Phthalide Ester of D(−)α-guanidino-p-hydroxybenzyl penicillin hydrochloride.

A solution of D(−)α-guanidino-p-hydroxyphenyl acetic acid hydrochloride (2.45 g., 0.01 M) in dimethylformamide (12 ml.) was added to a stirred solution of phthallyl-6-aminopenicillanate (3.48g., 0.01M) and dicyclohexylcarbodiimide (2.06 g., 0.01M) in dry methylene chloride (30 ml.) over a period of 5 minutes. The reaction mixture was stirred in a cold bath for 1½ hours, then in an ice-bath for 1 hour. The precipitate of dicyclohexylurea was filtered off, and the filtrate washed with N hydrochloric acid (2 × 30 ml.) and brine (30 ml.). The organic layer was separated, dried ($MgSO_4$) and added dropwise to stirred dry ether (500 ml.). The product (3.80 g., 66%) was filtered off washed with ether and dried in vacuo).

N.m.r $(CH_3)_2SO$ = δ 1.50 (6H.m. gemdimethyls); 4.53 (1 H.s. $C_3$ proton); 5.47 (2H.s. β-lactams); 5.63 (1H.d. α-proton); 6.76 (2H.d. p—OH aromatic protons); 7.24 (2H.d. p—OH aromatic protons); 7.44 (broad singlet NH protons )*; 7.60 (1H.s. HX of phthalide group); 7.90 (4H.m. phthalide aromatic protons); 9.00 (1H. NH proton)* p.p.m.

*Exchange with $D_2O$

EXAMPLE 26.

Phthalide Ester of DL α-guanidino-4-hydroxy-3-methylbenzyl penicillin hydrochloride.

The penicillin was prepared by dicyclohexylcarbodiimide coupling of DL-α-guanidino-4-hydroxy-3-methylphenylacetic acid hydrochloride (1.30g., 0.005 mol.) and phthallyl-6-aminopenicillinate (1.74g., 0.005 mol.) in the manner described in Example 25.

The yield of product was 1.40 g. (48%) N.m.r. $(CD_3)_2.SO$. δ = 1.57 (6H.m. gemdimethyls); 2.14 (3H.s. 3-methyl); 4.61 (1H.d. $C_3$proton); 5.54 (2H.d. β-lactam); 5.65 (1H.d. α-proton); 6.99 (3H.m. aromatic protons); 7.49 (4H.s. NM protons)*; 7.66 (1.H.s. —COOC$\underline{H}$=); 7.90 (4H.m. phthalide aromatic protons) 9.07 (1H. broad singlet. NH proton)*; 9.56 (1H.s. NH proton)* p.p.m.
*Exchange with $D_2O$

EXAMPLE 27.

Phthalide Ester of DL α-guanidino-4-hydroxy-2-methylbenzylpenicillin hydrochloride.

Following the procedure described in Example 25, DL-αguanidino 4-hydroxy-2-methylphenylacetic acid hydrochloride (1.30g., 0.005 mol.) was coupled to the phthalide ester of 6-aminopenicillinic acid (1.74g., 0.005 mol.) in the presence of dicyclohexylcarbodiimide. The yield of product was 1.20 g. (41%).

N.m.r. $(CD_3)_2SO$ δ = 1.52 (6H.d. gemdimethyls); 2.28 (3H.s. 2-methyl); 4.55 (1 H.d. $C_3$ proton); 5.66 (3H.m. β-lactam and α-proton); 6.61 (2H.m. aromatic protons); 7.19 (1H.m. aromatic proton); 7.47 (4H.m. NH protons)*; 7.60 (1H.s. —COOC$\underline{H}$=); 7.88 (4H.m. phthalide aromatic protons); 8.78 (1H. broad singlet. NH proton) p.p.m.

*Exchange with $D_2O$

EXAMPLE 28.

Phthalide ester of α-sulphobenzylpenicillin sodium salt.

Phthalide 6-aminopenicillanate (6.96g. 0.02 mol.) was dissolved in acetone (100 ml), cooled in an ice bath and treated with a 0.6M solution of α-sulphphenylacetylchloride in ether (33.3 ml., 0.02 mol.). The solution was adjusted to pH6.5 by the addition of N aqueous sodium hydroxide solution and stirred for 30 minutes. Phenylacetylchloride (2 ml) was added, the solution readjusted to pH6.5 then stirred for a further hour. The solvents were removed in vacuo and the residue diluted with water (100 ml.). This aqueous solution was washed with ether (2 × 200 ml.) and saturated with sodium chloride whereon an oil separated. The oil was collected and the aqueous phase extracted with ethyl acetate (2 × 100 ml.). The oil and ethyl acetate extracts were combined, washed with saturated brine (100 ml) and evaporated to dryness to give a yellow solid (6.28g.). This solid was dissolved in water (200 ml.), washed with ether (2 × 200 ml.), filtered through celite and the solution saturated with sodium chloride. The precipitated oil was extracted with n-butanol (200 ml.) and washed with water (2 × 50 ml.). Evaporation of the n-butanol solution yielded the phthalide ester of α-sulphobenzylpenicillin sodium salt (1.32g., 11.5%).

EXAMPLE 29.

a. Phthalide ester of α-(benzyloxycarbonyl)benzyl penicillin

Phthalide ester of 6-aminopenicillanic acid from the p-toluene sulphonate salt (5g.) was dissolved in acetone (50ml.) cooled to 0° and treated with triethylamine (1.4ml.). Monobenzylphenylmalonate (2.7g) was converted to the acid chloride by refluxing with thionyl chloride. excess thionyl chloride was removed by evaporation under reduced pressure and the residue dissolved in dry acetone (20ml.). This solution as added to the 6-aminopenicillanic acid ester and stirred for 1 hour at 0°. Filtration of the reaction mixture followed by evaporation under reduced pressure gave a residue which was dissolved in ethyl acetate (100ml.). The solution was washed with N hydrochloric acid (10ml.) and filtered to clarify. The filtrate was washed with N sodium bicarbonate (10ml.) followed by water (30ml.), dried over anhydrous magnesium sulphate and evaporated to give an oil. Trituration of this oil with di-isopropyl ether followed by petroleum ether gave a yellow solid in 50% yield.

N.m.r. $(CD_3)_2SO$: = 1.54 (6H.d. gem dimethyls) 4.53 (1H.m. $C_3$ proton) 5.15 (3H.m. benzylmethylene and α-proton) 5.50 (2H.m. β-lactam) 7.36 (10H.m phenyls) 7.60 (1H.s. —COOC$\underline{H}$=) 7.85 (4H.m. phthalide aromatic.)ppm.

b. Phthalide ester of α-carboxybenzylpenicillin

Phthalide ester of α-carboxybenzylpenicillin (2.9)) in methanol (100ml.) was added to a prehydrogenated mixture of 5% palladium on calcium carbonate (9g.) in ethanol (50ml.) and hydrogenation continued until no more hydrogen was absorbed. The mixture was filtered through Celite and evaporated to dryness. The residue was mixed with water (25ml.) and ethyl acetate (15ml.) and N sodium bicarbonate added to bring the pH to 7.0. The layers were separated and the aqueous phase was washed with ethyl acetate, acidified to pH 1.5 with N hydrochloric acid and extracted with ethyl acetate. Evaporation of the dried organic layer gave a yellow form which after trituration with petroleum ether gave a yellow solid 0.7g. (27%).

EXAMPLE 30.

Phthalide D(—)-α-amino-3-thienylacetamidopenicillanate.

A mixture of anhydrous D(—)-α-amino-3-thienylacetamidopenicillanic acid (11.83g. 0.033M.) and triethylamine (4.73ml. 0.033M.) was stirred in acetone containing 1% of water (300ml.) at ambient temperature for ½ hour. Potassium bicarbonate (3.5g) and 3-bromophthalide (7.10g. 0.033M.) were added at this stage to the penicillin salt and the mixture stirred at ambient temperature overnight. The triethylamine hydrobromide which precipitated during the course of the reaction was filtered off and the orange brown filtrate concentrated in vaccuo to 50–75 ml. and added to ethyl acetate (250ml.). The ethyl acetate layer was washed twice with 150ml. portions of 2% aqueous sodium bicarbonate and twice with 100ml. portions of water. The organic layer was mixed with water (200ml.) and the mixture vigorously stirred at pH 2.0–2.5 for 0.75 hour. The ester was salted out into the ethyl acetate layer by the addition of sodium chloride and the organic layer was separated and dried over anhydrous magnesium sulphate. After filtration the ethyl acetate was diluted with an equal volume of diethyl ether which precipitated the ester as a white amorphous hydrochloride salt in 42% yield, which was washed well with diethyl ether.

Hydroxylamine assay = 90.7%
$C_{22}H_{22}N_3S_2O_6Cl$ requires C,50.40; H,4.21; N8.03;S,12.3;Cl,6.78. Found C,49.79; H4.16, N, 7.57; S12.41;Cl,6.71.

i.r. (KBr disc) strong bands at 1775 $cm^{-1}$ 1695 $cm^{-1}$ 1284 $cm^{-1}$ 1212 $cm^{-1}$ 1150 $cm^{-1}$ 975 $cm^{-1}$ n.m.r. $(CD_3)_2SO/D_2O$ = 8.0–7.10 (8H.m. aromatics and COOC$\underline{H}$—O— ) 5.15 (2H.m. β-lactam protons) 5.28 (1H. broad singlet. α-proton) 4.55 (1H.s. C$_3$ proton 1.50 (6H. d. gem dimethyls.)

EXAMPLE 31.

PHTHALIDE ESTER OF CLOXACILLIN(6-[3-O-chlorophenyl-5-methyl isoxazole-4-carbamido] penicillanic acid)

Sodium cloxacillin (14.3 g. 0.03M) was dispersed in dry dimethylformamide (400 mls). To the stirred mixture, 3-bromophthalide (6.39 g 0.03M) was added in one portion and the reaction was continued for 2 hours at ambient temperature.

The resulting mixture was then poured into ice water; the white precipitate obtained was filtered and washed extensively with water, and finally freeze dried to yield a white amorphous solid. (15.2 g. 89%). Biochromato- graphic evidence showed the product to be the desired ester ($R_f$ 0.95)

A small sample of the product was further purified by dissolving in ethanol and pouring the solution into excess petroleum ether (40°–60° C)

$C_{27}H_{22}O_7N_3SCl$ required: C 57.20; H 3.86; N 7.41 S 5.59; Cl 6.26 found C 56.40; H 3.59; N 7.13 Cl 6.53 n.m.r. $[(CD_3)_2SO]$

δ 8.41 (1 H. d N$\underline{H}$ CO Exchangeable $D_2O$)
δ 7.84 (4. H. m. phthalide aromatics)
δ 7.60 (1.H. s. CO.O C$\underline{H}$)
δ 7.54 (5.H. s. phenyl aromatics)
δ 5.44–5.80 (2.H. m. β lactams)
δ 4.55 (1.H.s. C—3 proton)
δ 2.68 (3.H.s. C$\underline{H}_3$on isoxazole ring)
δ 1.49 (6.H.s. gem dimethyls)

i.r. (Nujol) strong bands at 1780 $cm^{-1}$, 1670 $cm^{-1}$, 980 $cm^{-1}$.

EXAMPLE 32.

Preparation of phthalide ester of 6 [D-)α-amino-(p-hydroxyphenylacetamido ] penicillanic acid]

METHOD.

A solution of phthalide 6-aminopenicillannic acid p-toluene-sulphonate (10.4 g : 0.02 M) in ethyl acetate (500 ml) was thoroughly shaken with 2% sodium bicarbonate solution (314ml), and then with water (225 ml containing 7 ml of 2% sodium bicarbonate solution). The organic layer was dried over magnesium sulphate, filtered and the solvent evaporated off in vaccuo to give a foam.

A suspension of enamine protected 6O -amino-p-hydroxy - phenyl acetic acid sodium salt (5.74 g : 0.04 M) in dry ethyl acetate (100 ml) was cooled to —15° C with stirring. N-methylmorpholine (2.07 ml) and ethyl-chloroformate (3.81 ml : 0.04 M) were added, stirring was continued at 15° C for 6 minutes.

An ice-cold solution of the 6-aminopenicillanic acid ester in dry ethyl acetate (100 ml) was then added, and the reaction mixture stirred at —12° to —14° C for 10 minutes, and then at room temperature for ½ hour.

The reaction mixture was washed with N/2 sodium bicarbonate solution (40 ml), water (2 × 20 ml) and then the organic layer was dried over magnesium sulfate. The magnesium sulphate was filtered off and the solvent removed in vacuo to give a yellow foam.

The foam was dissolved in acetone (80 ml) and water (80 ml). The solution was vigorously stirred and the pH adjusted to 2.5 with 5 N hydrochloric acid. The acetone was evaporated off in vacuo and the aqueous extracted with ethyl acetate (80 ml). The organic layer was then diluted with petrol 40°–60° (70 ml) and extracted with water at pH 3 (100 ml).

The combined aqueous extracts were saturated with solid sodium chloride and the oily upper layer removed. The oil was dissolved in iso-propanol (50 ml) and filtered. The solution was then dripped into excess ether, and the resulting solid was then filtered off and dried.

Yield = 1.5g = 14.0 % hydroxylamine assay = 94.9% I.R. spectrum showed inter alia strong bands at: (nujol mull)

985 $cm^{-1}$, 1220 $cm^{-1}$, 1315 $cm^{-1}$, 1685 $cm^{-1}$, 1760 $cm^{-1}$ and 1780 $cm^{-1}$ N.M.R. spectrum in $(CD_3)_2SO + D_2O$ showed :-
δ = 1.46 (singlet = 6H = gem di methyls)

$\delta = 4.55$ (singlet = 1H = $C_3$ proton)
$\delta = 5.20$ (singlet = 1H = HO Ph CH, α-proton)
                                    |
                                   $NH_3$ $\delta = 7.20$ to 8.00 (multiple bands 32 9H = HO-Ph-CH— +phthalide aromatics)

EXAMPLE 33.

a. 3-chloro-3-methylvalerolactone.

Prepared by the method of Wolffe, Annalan 229 271 in 78% yield.

b. Preparation of 3,3,methylvalerolactone ester of 6[D(−)(N-methoxy-carbonylpropene-2-yl)-2-aminophenylacetamido]penicillanic acid.

The potassium salt of 6[D(−)N-methoxycarbonylpropen-2-yl)— α-aminophenylacetamido]penicillanic acid (10.1g 0.02m) was dispersed in dry acetone (250ml) and chilled to 0° C. Nitrogen was bubbled slowly through the mixture and freshly prepared 3-chloro-3-methyl-valerolactone (2.7g. 0.02m.) together with a catalytic amount of sodium iodide were added in one portion. The reaction was continued under nitrogen at 0° C for two hours and then allowed to warm to room temperature and maintained for a further 5 hours.

The solvent was evaporated in vacuo and the residue dissolved in ethyl acetate and washed successively with water, sodium bicarbonate solution (2% w/v) and water. The solution was then dried over anhydrous magnesium sulphate, filtered and the solvent evaporated in vacuo to yield a yellow syrup. A white amorphous solid was obtained after trituration with petroleum ether (40—60°). Yield 2.3g (21%).

c. Preparation of 3,3methylvalerolactone ester of 6[D(−) α-amino-phenylacetamido]penicillanic acid, hydrochloride.

The ester prepared in (b) above (3.2g. 0.0057m) was dissolved in acetone (200ml) and the solution was diluted with water 150ml). The pH of the solution was reduced to 2.5 with dilute hydrochloric acid (5N) and maintained at this value for 20 mins.

The acetone was then evaporated in vacuo leaving a white precipitate in the aqueous phase. The residual aqueous mixture was extracted with ethyl acetate (160ml) and the phases were separated. The organic phase was diluted with petroleum ether (40°-60°) (40ml) and re-extracted with water at pH 3.0.The aqueous extract was separated and combined with the aqueous phase first obtained. The combined phases were then treated with solid sodium chloride (80g) and the saturated solution was stirred vigorously. An oily layer separated which was dissolved isopropanol (75ml). A small amount of white solid was filtered off and discarded. The filtrate was then poured into excess anhydrous ether (1500ml) yielding a white flocculant precipitate. The precipitate was filtered, washed with anhydrous ether and petroleum ether (40°-40°) and dried.

Yield 22mg. (9%).

EXAMPLE 34.

5,6-Dimethoxyphthalide D,L-α-Amino-3-thienylmethyl Penicillanate, HCl.

D,L-α-amino-3-thienylmethylpenicillin(7.1g. 0.02m.) and triethylamine (2.02g. 2.8ml. 0.02m) were mixed with acetone (140ml) containing 1% water. After stirring the suspension for one-half hour potassium bicarbonate (2g. 0.02m) and 3-bromo-5,6-dimethoxyphthalide (5.46g 0.02m) were added and the mixture stirred vigorously at room temperature for 4 hours.

The mixture was filtered through Celite and evaporated at room temperature to about 30mls. Ethyl acetate (200ml) was added and the solution washed with 2% sodium bicarbonate solution (2 times with 40mls), water (40ml) and then water (60ML) was added to the ethyl acetate layer and, with vigorous stirring, the pH was maintained at 1.8 by dropwise addition of 5N hydrochloric acid. The organic layer was separated, dried over anhydrous magnesium sulphate and poured into stirring dry ether. The solid was filtered, washed and dried.

A further quantity of solid was obtained by salting the acidic aqueous phase and pouring a propanolic solution of the resultant oil into ether.

Yield 2.5g. (21.4%)

hydroxylamine essay: 106.3% i.r. spectrum: (KBr disc) Strong bands at 1750 cm$^{-1}$ 1600 cm$^{-1}$ 1502 cm$^{-1}$ 1341 cm$^{-1}$ 1288 cm$^{-1}$ 976 cm$^{-1}$ n.m.r. spectrum $(CD_3)_2SO$: $\delta = 1.51$ (6H.m.gem dimethyls) 3.93 (6H.s.-$OCH_3$) 4.53 (1H.s.$C_3$ proton) 5.27 (1H.broad s.)sharpening on $D_2O$ exchange- α proton of thienylmethyl group) 5.57 (2H.m.β-lactams) 7.48 (6H.m.thienyl and phthalide aromatics and phthalide proton) 9.3—8.7 (4H.diffuse bands removed on $D_2O$ exchange —CONH—and —$NH_3{^+}$)

EXAMPLE 35

Phthalide 6-[(hexahydro-1H-azepin-1-yl)-methyleneamino]-penicillanate, hydrochlorine.

N-formylhexamethyleneimine (6.35 g) was dissolved in dry diethyl ether (200 ml.). Oxalyl chloride (4.25 ml.) in dry diethyl ether (30 ml.) was added dropwise to the ethereal solution of the imine and the mixture stirred at 0°-5° for one-half hour and at ambient temperatures for 6 hr. The precipitated amide chloride was collected and washed well with dry ether and placed immediately in a dessicator containing $P_2O5$.

Phthalide 6-aminopenicillanate tosylate (11.44 g ; 0.025 M — prepared via Delft cleavage of phthalide ester of pencillin G as described previously ) was suspended in ethyl acetate (650 ml.) under continuous stirring and cooling in an ice-bath. A solution of ice-cold 2% sodium bicarbonate (450 ml.) was added and the organic layer separated and shaken with ice-water (500 ml.) containing 2% sodium bicarbonate (10 ml.) and then dried over anhydrous magnesium sulphate. After filtration the solvent was evaporated in vacuo to yield the phthalide 6-aminopenicillanate as a foam. The foam was dissolved in chloroform (75 ml.) and triethylamine (7.0 ml) was added dropwise at −30° −40° C. The chlorohexamethyleneiminium chloride (4.8g; 0.025M) in chloroform (35 ml.) was added dropwise at a temperature of ca. −20° C. After standing at −20° C for one-half hour the temperature was raised to 0° within one-half hour. The solution was evaporated to dryness in vacuo and the residue stirred with diethyl ether (300 ml.). Undissolved triethylamine hydrochloride was filtered off and the solvent again evaporated in vacuo and the residue dissolved in isop (25 ml.). The solution was cooled to 0° C with stirring and a solution of 8.5 N hydrogen chloride in isopropanol (2.5 ml.) was added. The product precipatated in 46% yield and was washed well with, dry diethyl other. The product was reprecipitated from methanol - diisopropyl ether with an 85% recovery.

Biochromatography :
1. single spot (with B.Sub ) at $R_f = 0.88$ (only after spraying with phenyl acetyl chloride).
2. single spot (with E.coli) at $R_f = 0.90$. (which disappears on spraying with phenyl acetyl chloride).

i.r. (KBr) strong bands at :
2940 $cm^{-1}$ 1780 $cm^{-1}$ 1680 $cm^{-1}$ 1460 $cm^{-1}$ 1355 $cm^{-1}$ 1282 $cm^{-1}$ 1195 $cm^{-1}$ 1145 $cm^{-1}$ 985 $cm^{-1}$ 75 $cm^{-1}$ n.m.r. [$(CD_3)_2$ $SO/D_{20}$]: $\delta = 7.85$(4H. s. phthalide aromatics);
$\delta = 7.62$(1H. S. —COOCH — OCO); $\delta = 5.63$(1H.s. C-5 proton);
$\delta = 5.10$ (1H.m. C-6 proton); $\delta = 4.78$(1H.s. C-3 proton);
$\delta = 3.68$(4H.broad multiplet:

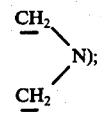

$= 1.64$ (14H.m.gem dimethyls and protons of azepin ring.)

Hydroxylamine assay = 74.9%.

EXAMPLE 36 a. Preparation of chlorodimethyformiminum chloride

Method

Oxalyl chloride (6.35g; 0.05 M) dissolved in dry ether (50+) was slowly added to a solution of dimethylformamide (3.65g : 0.05M) at 0° C. The precipiate formed was filtered almost immediately and washed with dry ether. The solid was used immediately for the reaction below.

b. Preparation of phthalide 6-(N,N-dimethylformamidine-N'-)-penicillinate hydrochloride Method A solution of phthalide 6-aminopencillanic acid p-toluene-sulphonate salt (10.40g.: 0.02M) in ethyl acetate (500 ml.) was thoroughly washed with 2% sodium bicarbonate solution (314 ml.) and water (250 ml. containing 7ml. of 2% sodium bicarbonate solution). Dried over magnesium sulphate, filtered and the solvent removed in vacuo to give a foam.

The foam was dissolved in chloroform (75 ml.) and to it was added triethylamine (6.1 ml.) at −30° to −40° C. To the stirred solution was added chlorodimethylformiminium chloride (2.56g.: 0.02M) in chloroform (40 ml.). The temperature was allowed to rise to 0° C within 1 hour. The solution was then evaporated to dryness in vacuo and the residue treated with ether (300 ml.), and filtered. The ether was evaporated off in vacuo and the gun dissolved in isopropyl alcohol (20 ml.). The solution was cooled to 0° C. with stirring and 8.5N hydrogen chloride in isopropyl alcohol (2 ml.) was added. A solid was precipitated out with ether.

Yield = 1.6 g = 18.2%

$\dfrac{\text{Bio-chromatogram}}{\text{(After spraying)}} R_f = 0.84$

I.R. spectrum (nujol mull) showed inter alia strong bands at :
760 $cm^{-1}$, 980 $cm^{-1}$, 1215 $cm^{-1}$, 1700 $cm^{-1}$, 1740 $cm^{-1}$ and 1780 $cm^{-1}$ N.M.R. spectrum in $(CD_3)_2SO + D_2O$ showed :
$\delta = 1.50$ (doublet = gem dimethyls)
$\delta = 3.20$ (doublet = N,N-dimethyls)
$\delta = 5.21$ (doublet = $C_3$ proton)
$\delta = 5.62$ (multiplet = $\beta$-lactam protons)
$\delta = 7.61$ (singlet = phthalide CH)
$\delta = 7.70 — 8.10$ (broad multiplet = phthalide aromatics

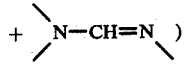

)

EXAMPLE 37

$\alpha,\beta$-Bis Phthalide ester Carbenicillin ( (d)$\alpha$-Carboxyphenylacetamido penicillanic acid)

The disodium salt of carbenicillin (6.33g.; 0.015M) was dispersed in dimethylformamide (100 ml.) of 0° C. 3-Bromophthalide (6.39g; 0.03M) was added in one portion to the stirred suspension and allowed to react for a further one-half hour at 0° and then for a period of 2 hours at ambient temperature.

The reaction mixture was poured into ice-cold water (1000 ml.) and the diester which precipitated out of the aqueous solution extracted into ethyl acetate (250 ml.) and washed with 2% sodium bicarbonate (2 × 250 ml.) and water (2 × 250 ml.) and then dried over anhydrous magnesium sulphate. After filtration the ethyl acetate was concentrated in vacuo to ca 75ml. and diethyl ether (100 ml.) was slowly added to the stirred ethyl acetate solution to precipate the diphthalide ester as a white amorphous solid in 85% yield.

Recrystallisation from ethanol gave the product as a white crystalline solid in 69% yield.

I.R. (XBr disc) strong bands at:
1780 $cm^{-1}$ 1685 $cm^{-1}$ 1510 $cm^{-1}$ 1358 $cm^{-1}$ 1282 $cm^{-1}$ 1215 $cm^{-1}$
1148 $cm^{-1}$ 1050 $cm^{-1}$ 975 $cm^{-1}$ 750 $cm^{-1}$ N.M.V. [$(CD_3)_2 SO/D_2O$]$\delta = 7.38$ (8H. s. both phthalide aromatics); $\delta = 7.58$ (1H. s. COO C$\underline{H}$ -) ; $\delta = 7.50$ (1H. s. COOC$\underline{H}$—) $\delta = 7.37$ (5H.s. phenyl aromatics); $\delta = 5.50$ (2H. $\alpha$ $\beta$-lactams aromatics) $\delta = 5.17$ (1H. s. benzyl proton); $\delta = 4.52$ (1H. s. C-3 proton); $\delta = 1.44$ (6H. d. gem-dimethyls). Single spot on biochromatogram at $R_f = 0.90$.

$C_{32}H_{26}N_2O_{10}S$ requires C, 60.95; H, 4.03; N, 4.44; S, 5.08. found C, 60.8; H, 4.06; N, 4.37 S, 5.04.

Hydroxylamine assay = 209.1%.

EXAMPLE 38

$\alpha,\beta$-Bisphthalide ester of 6[D-$\alpha$-carboxy-3-thienylacetamido]Penicillanic acid The disodium salt of D-$\alpha$-carboxy-3-thienylacetamido penicillanic acid (8.3g ; 0.02M) was dispersed in dry dimethylformamide (100 ml.) at 0° C.

3-Bromophthalide (8.52g; 0.04M) was added in one portion to the stirred suspension and allowed to react for a further one half hour at 0° and then for a period of 2 hours at ambient temperatures.

The reaction mixture was poured into ice-cold water (1000 ml.) and the solid which precipitated immediately out of the aqueous solution was extracted into ethyl acetate (250 ml.) and washed with 2% sodium bicarbonate (2 × 250 ml.) and water (2 × 250 ml.) and then dried over anhydrous magnesium sulphate. After filtraton the ethyl acetate was concentrated in vacuo to ca 70 ml. and diethyl ether (100 ml.) was slowly added to the stirred ethyl acetate solution to precipitate the diphthalide ester as a white amorphous solid in 90% yield. Recrystallisation from ethanol gave the product as a white crystalline solid in 70% yield.

i.r. (Kbr disc) strong bands at: 1780 $cm^{-1}$ 1688 $cm^{-2}$ 1510 $cm^{-2}$ 1358 $cm^{-1}$ 1282 $cm^{-1}$ 1215 $cm^{-1}$ 1148 $cm^{-1}$ 1050 $cm^{-1}$ 975 $cm^{-2}$ 750 $cm^{-1}$ N.M.R. $\delta[(CD_3)_2SO/D_{20}]\delta = 7.85$ (8H. broad singlet: both phthalide aromatics),]$\delta = 7.58 - 7.15$ (5H. m. thienyl aromatics and 2 proton in a COO C$\underline{H}$-O-CO environment); $\delta = 5.50$ (2H.m.$\beta$-lactam protons); $\delta = 5.28$ (1H, s. benzyl. proton); 4.54 (1H.s. C-3 proton); $\delta = 1.45$ (6H. s. benzyl proton); 4.54 (1H.s. C-3 proton); $\delta = 1.45$ (6H, d. gen-dimethyls).

Single spot on biochromatogram at $R_f = 0.90$.

$C_{30} E_{24}N_2O_{10} S_2$ requires: C, 56.57; H,3.77; N,4.40; S, 10.06 found: C, 56.44; H,3.83; N,4.09 S, 9.73.

Hydroxylamine assay = 200.0%.

EXAMPLE 39

Bis Crotono Lactonyl Ester of 6[D-$\alpha$-carboxy-3-thienyl acetamido]penicillanic acid

Method

The disodium salt of 6[D-$\alpha$-carboxy-3-thienylacetamido]penicillanic acid (8.3g. 0.019 m.) was dispersed in dry dimethyiformamide (100 ml.) and the suspension was chilled to 0° C. Crude 3-bronon crotonolactone (8.0 g. 0.04m assuming 80% purity) was then slowly added to the stirred mixture over a period of some 5 minutes. The cooling bath was then removed and the reaction was continued at ambient temperature for 2 hours.

The reaction mixture was poured into ice-water (600 mls.) and the brown solid obtained was filtered and washed with water (pH 3.0). The residue was then treated with chloroform (400 ml.) and the insoluble materials filtered. The resulting brown coloured filtrate was washed with water (3 × 150 mls), dried (MgSO$_4$), filtered and the solvent evaporated in vacuo to yield a brown foam. A brown amorphous solid was obtained following trituration with pertroleum ether (40°–60° C). Yield 5.8 g. (56% based on penicillin).

The product was further purified by redissolving the compound in chloroform (50 mls. ) and pouring the solution into excess cyclohexane (1000 mls.) n.m.r. (CDCl$_3$/D$_{20}$).

$\delta = 7.38$ (4H. m. 2 ×0.C$\underline{H}$O. plus 2 × CH=CH-CO $\delta = 7.18$ (1H, m. CH=CH-5)

$\delta = 6.34$ (2H. m. CH=CH-CO $\delta = 5.55$ (2H, m. $\beta$-lactams)

$\delta = 4.85$

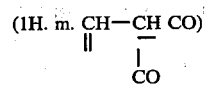

$\delta = 4.47$ (1H. m. C-3proton)

$\delta = 1.52$ (6H. s. gem dimethyls)

I.R. (KBr disc) strong bands at 1785 $cm^{-1}$ (shoulder 1760 $cm^{-1}$), 1675 $cm^{-1}$, 1085 $cm^{-1}$, 1005 $cm^{-1}$.

Biochromatogram: $R_f$ 9.95 and $R_f$ 0.6

EXAMPLE 40

Combination salt of 6-[3- (2-chloro-6fluorophenyl)-5-methyl isoxazole-4-carbamido ]penicillanic acid (Flucloxacillin) and phthalide D(−)$\alpha$-amino-phenylacetamidopenicillanate.

A solution of the sodium salt of flucloxacillin (4.76g ; 0.01M) in water (100 ml.) was mixed with a solution of phthalide D(−)-$\alpha$-amino-phenylacetamidopenicillanate, hydrochloride in water (150 ml.) at ambient temperatures. Immediately a white amorphous solid precipitated which was collected, washed well with cold water and dried over P$_2$O$_5$in vacuo ti give an 85% yield of the combination salt.

Hydroxylamine assay = 182.5%

$C_{43}H_{40}N_6S_2O_{11}Cl$ F requires C,55.22; H4.29; N,9.00; S,6.86

C,53.56; H,4.45; N,8.42; S,6.18.

I.R. (KBr disc) strong bands at 1780 $cm^{-1}$ 1670 $cm^{-1}$ 1600 $cm^{-1}$ 1500 $cm^{-1}$ 1285 $cm^{-1}$ 978 $cm^{-1}$ 895 $cm^{-1}$.

N.M.R. [(CD$_3$)$_2$ SO/D$_{20}$]:

$\delta = 7.85$(4H.m. phthalide aromatics);

$\delta = 7.60$ (1H. s. -CO.O C$\underline{H}$-);

$\delta = 7.52$ (3H. s. Fluclox. aromatics);

$\delta = 7.46$ (5H. m. phenylaromatics);

$\delta = 5.47$ (4H, m. $\beta$-lactam protons);

$\delta = 5.00$ (1H. s. $\alpha$-proton from ampicillin moiety);

$\delta = 4.53$ (1H. s. C-3proton from ampicillin moiety);

$\delta = 4.12$ (1$\underline{H}$. s. C-3 proton from flucloxacillin moiety);

$\delta = 2.71$ (3H. s. isoxazole 5-methyl);

$\delta = 1.48$ (12H. m. gem dimethyls).

EXAMPLE 41

Salt of Flucloxacillin and Phthalide 6-[(hexahydro-1H-azepin-1-yl) methylereamino]-penicillonate A 10% aqueous solution of the sodium salt of flucloxacillin (4.76 g; 0.01 M) and a 10% aqueous solution of phthalide 6-[(hexahydro-1H-azepin-1-yl) methyleneamino]penicillanate, hydrochloride (4.93g; 0.01H) were mixed at ambient temperatures. Immediately a white amorphous solid precipitated which was collected, washed well with cold water and dried over P$_2$O$_5$ in vacuo to give a 67% yield of the combination salt. Biochromatogram contained one spot at $R_f = 0.70$ (Flucloxacillin) (before spraying with phenylacetyl chloride) and 2 spots after spraying one at $R_f = 0.89$ (amidino ester) and the other at $R_f = 0.07$ (Flucloxacillin).

I.R. (Nujol) strong bands at: 1775 $cm^{-1}$ 1675 $cm^{-1}$ 1460 $cm^{-1}$ 1378 $cm^{-1}$ 980 $cm^{-1}$ 910 $cm^{-1}$

EXAMPLE 42

Phthalide 7-(2-thienylacetamido)cephalosporanate (cephalothin ester)

3-Bromophtalide (5.37 g; 0.025 M) was added to a stirred suspension of 7-(2-thienyldacetamido)cephalosporanate (10.45 g; 0.025M) in dimethylformamide (75 ml.) of 0° and the mixture reacted for one-half hour at 0°C and then for a further 1 hour at ambient temperatures, by which time a clear brown solution had formed. The reaction solution was added to ice cold water (ca. 1500 ml.) and stirred for 20 minutes and the creamy/white solid which precipitated collected and washed well with cold water and then freeze dried to give 10.5 g. of an amorphous powder, biochromatogram indicated two spots one major at $R_f = 0.39$ (unreacted cephalothin).

Hydroxylamine assay = 73.6%

The unreacted cephalothin was removed from the solid by dissolving it in the minimum amount of ethyl acetate and washing twice with 2% sodium bicarbonate and water. The organic layer was dried over magnesium sulphate (anhydrous) and the solvent evaporated in vacuo to yield a sticky solid which solidified upon trituration with a mixture of diethyl ether and petroleum ether, b.p. 40–60°. Yield 65%. The n.m.r. spectrum indicated that the major component was the $\Delta 3$ isomer with approximately 10—20% of the $\Delta 2$ isomer. A purer sample was obtained by recrystallisation from isopropanol, although the recovery was only 50%.

Hydroxylamine assay = 74.1%

Single spot on biochromatogram at $R_f = 0.90$.

$C_{24}H_{20}N_2S_2O_8$ requires : C, 54.49; H. 3.79; N,5.29; S,12,10 found: C,54.11; H, 3.98; N, 5.02; S,12,30.

N.M.V. [$(CD_3)_2SO/D_{20}$]: $\delta = 9.14$ (1H. d. CONH); $\delta = 7.85$ (4H.m. phthalide aromatics); $\delta = 7.65$ (1H.m. COO CH—OCO—);

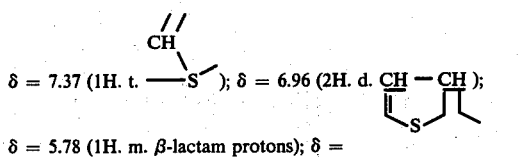

$\delta = 7.37$ (1H. t. —S ); $\delta = 6.96$ (2H. d. CH — CH );

$\delta = 5.78$ (1H. m. $\beta$-lactam protons); $\delta = 5.08$ (3H. m. $\beta$-lactam proton and

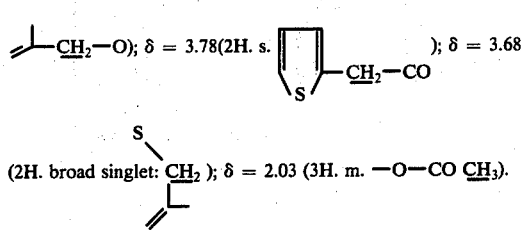

—CH$_2$—O); $\delta = 3.78$(2H. s. ); $\delta = 3.68$ (2H. broad singlet: CH$_2$ ); $\delta = 2.03$ (3H. m. —O—CO CH$_3$).

I.R. (KBr): strong bands at: 3280 cm$^{-1}$ 1740 cm$^{-1}$ 1655 cm$^{-1}$ 1620 cm$^{-1}$ 1425 cm$^{-1}$ 1405 cm$^{-1}$ 1370 cm$^{-1}$ 1350 cm$^{-1}$ 1240 cm$^{-1}$ 1030 cm$^{-1}$ 1020 cm$^{-1}$ 708 cm$^{-1}$.

EXAMPLE 43.

1.3,Dioxalan-2-one-4-yl ester of Benzylpenicillin.

Method.

The sodium salt of benzylpenicillin (14.9g, 0.04m) was dispersed in dry dimethylformamide (150 mls) and the solution chilled to 0°C. Freshly distilled 4-chloro-1,3,Dioxalan-2-one (4.92g. 0.04m) was added to the stirred solution, together with a catalytic amount of sodium iodide, and the mixture was maintained at 0°C for 30 minutes. The reaction mixture was then allowed to warm to room temperature and stirring was continued for 16 hours.

The reaction medium was then poured into ice water and yielded a brown coloured emulsion. A small quantity of solid sodium chloride was added and the aqueous phase was extracted with ethyl acetate (2 × 250 mls). The ethyl acetate phase was then washed with dilute sodium bicarbonate solution (2 w/v), and water, and finally dried (MgSO$_4$). The mixture was filtered and the solvent evaporated in vacuo to yield a yellow syrup. The syrup was dissolved in isopropanol and a solid was precipitated with excess petroleum ether (40–°C). A white flocculent precipitate was initially apparent which turned brown on prolonged exposure to air. Biochromotographic evidence showed the product to be the desired ester (Rf 0.95) containing a trace impurity of penicillin G (Rf 0.60).

$C_{19}H_{20}O_7N_2S$ Requires C54:20; H 4.74; N 6.66. found: C52.00; H 4.56; N 6.32

| $C_{19}H_{20}O_7N_2S$ Requires | C54.20; H 4.74; N 6.66. |
| --- | --- |
| | found: C52.00; H 4.56; N 6.32 |
| n.m.r. (CDCl$_3$) | |
| $\delta$ 7.33 | (5H.s. aromatic protons + 1.H. equivalent due to impurity). |
| $\delta$ 6.70 | (1H.m. CO.O.CH O) |
| $\delta$ 6.15 | (1H.d. NHCO - exchangeable D$_2$O). |
| $\delta$ 5.75–5.4 | (2H.m. $\beta$-lactams). |
| $\delta$ 4.80–4.20 | (3.H.m. C-3 proton +CH$_2$-O). |
| $\delta$ 3.64 | (2.H.S. Ph CH$_2$) |
| $\delta$ 1.5 | (6.H.s. gem dimethyls). |

EXAMPLE 44.

Phthalide exter of phenoxymethylpenicillin thio acid.

Method.

The potassium salt of phenoxymethylpenicillin (2.1g, 0.005m) was dispersed in dry dimethylformamide (25 mls) at ambient temperature. To the stirred suspension, 3-bromo phthalide (1.06g 0.005m) was added and the reaction was continued for 60 minutes.

The reaction mixture was then poured into ice water (100 mls) and the white precipitate obtained was washed extensively with water, filtered and dried using a freeze-drier. Yield 2.25g (90%)

$C_{24}H_{22}O_6N_2S_2$ requires C 57.83; H 4.42; N 5.62 S 12.85 found: C 57.73; H 4.93; N 5.51 S 12.57 n.m.r.

$\delta$ 8.83 1.H.d. NHCO exchangeable D$_2$O)

$\delta$ 8.1–7.65 (4.H.m. phthalide aromatic protons).

$\delta$ 7.5–6.75 (6.H.m. 5 phenyl protons + S CH O)

$\delta$ 5.85–5.55 (2.H.m. $\beta$-lactams)

$\delta$ 4.65 (2.H.s. O CH$_2$)

$\delta$ 4.55 (1.H.d. C-3 proton)

$\delta$ 1.80–1.30 (6.H.m. gem dimethyls). i.r. (KBr) strong bands at 1778 cm$^{-1}$, 1690 cm$^{-1}$, 1285 cm$^{-1}$ and 970 cm$^{-1}$.

EXAMPLE 45

PREPARATION OF 2-THIOPHALIDE ESTER OF BENZYLPENICILLIN

Method

A suspension of sodium salt of benzylpenicillin (7.12g : 0.02m) was stirred in dry D.M.F. (50 ml.) at 0° C. To this was added, in one portion, 3-bromo-2-thiophthalide (4.58g. : 0.02m) in dry D.M.F. (20 ml.). The reaction mixture was allowed to warm to room temperature and stirred for a further 2 hours. After this time it was poured into 2 liters of ice-water. The aqueous was then extracted with chloroform (3 × 200 ml). The chloroform extracts were combined, dried over magnesium sulphate, filtered and the solvent removed in vacuo. The gum was taken up in methanol (100 ml) and treated with charcoal. The solution was filtered and the solvent evaporated off in vacuo. The pale yellow gum was triturated with petrol 40°–60° and a solid obtained, which was filtered off and dried.

Yield = 1.3g = 13.3% Bio-chromatogram Rf = 0.95

I.R. Spectrum (nujol mull showed inter alia strong bands at: 908 cm$^{-1}$, 1240 cm$^{-1}$, 1650 cm$^{-1}$, 1690 cm$^{-1}$ and 1778 cm$^{-1}$ N.M.R. Spectrum in $(CD_3)_2SO + D_2O$
= 1.55 (multiplet = 6H = gem di-methyls)
= 3.62 (singlet = 2H = Ph-CH$_2$ CONH—)
= 4.68 (doublet = 1H = C$_3$ proton) = 5.55 (singlet = 2H = β - lactam protons)
= 7.33 (broad band = 5H = PhCH$_2$CONH—)
= 7.52 (doublet = 1H = phthalide CH)
= 7.88 (broad band = 4H = phthalide aromatic protons)

| Analytical Data | | | | |
|---|---|---|---|---|
| Required: | C 59.70; | H 4.57; | N 5.52; | S 13.25 |
| Found: | C 57.54 | H 4.69 | N 5.60 | S 12.96 |
| | 57.44 | 4.58 | 5.59 | 12.80 |

EXAMPLE 46.

a. 3-Bromophthalide
[3-Bromo-1-(3H)-Isobenzofuranone]

Phthalide (10.0 g; 0.075 moles) and N-bromosuccinimide were refluxed in dry carbon tetrachloride (200 ml.) in the presence of a catalytic amount of α-azo-isobutyronitrile for 3–4 hours. The end of the reaction was indicated by the disappearance of N-bromosuccinimide from the bottom of the reaction vessel and the accumulation of succinimide at the top. The succinimide was removed by filtration and the filtrate concentrated in vacuo to 15–20 ml. Cooling of this concentrate followed by filtration gave 13.0 g. (81% yield) of crude 3-bromophthalide, m.p. 75°–80°, as a white crystalline solid. The product was recrystallised from cyclohexane as colourless plates, m.p. 78°–80° with a 95% recovery.

N.m.r. (CCl$_4$)Br— δ = 7.67 (4H.m. aromatic), δ = 7.38 (1H.s. CH—)

b. D(—)α-aminobenzylpenicillinphthalide ester, hydrochloride

Anhydrous D(—)α-aminobenzylpenicillin (17.5; 0.05 mole) and triethylamine (7.10 ml; 1 equiv.) were mixed with acetone containing 1% of water (350 ml.). After one-half hour potassium bicarbonate (5 g) and 3-bromophthalide (10.65 g; 0.05 mole) were added and the mixture stirred at room temperature for 4 hours. After filtration, the filtrate was concentrated in vacuo to about 75 ml, ethyl acetate (500 ml) was added and the resulting solution washed within a 2% aqueous solution of sodium bicarbonate (2 × 100 ml) followed by water (2 × 100 ml). Water (150 ml) was added to the ethyl acetate solution, and, with vigorous stirring, 1N hydrochloric acid was added drop by drop until the pH of the aqueous phase was 2.5. The ethyl acetate layer was separated and dried over anhydrous magnesium sulphate. Ether was then added to the clear yellow ethyl acetate filtrate until no further precipitation of a white amorphous solid occurred. The product was collected (7.8 g; 28.8%). Further material (0.08 g; 3.0%), was obtained from the aqueous layer as follows. To the aqueous layer, n-butanol (750 ml) was added and the resulting mixture was evaporated in vacuo until all the water was removed. The resulting butanolic solution was poured into ether (2000 ml) whereby an amorphous precipitate separated. Combined yields were 31.8%.

The I.R. spectrum (KBr) contains inter alia strong bonds at:
1778 cm$^{-1}$ 1682 cm$^{-1}$ 1500 cm$^{-1}$ 1285 cm$^{-1}$
1149 cm$^{-1}$ 978 cm$^{-1}$ 752 cm$^{-1}$ 697 cm$^{-1}$ n.m.r. ((CD$_3$)$_2$SO/D$_2$O): ,δ = 7.88 (4H.m. phthalide aromatics(; δ = 7.60 (1H.s. —CO.OCH—); δ = 7.48 ](5/6H.m. aromatic); δ = 5.50 (2H.m. β-lactams); δ = 5.16 (1H.s. α-proton); δ = 4.54 (1H.s. C$_3$ proton); δ = 1.45 (6H.d. gem-dimethyls). The purity as assessed by hydroxylamine and crysteine assays was 92.4% and 86.5% respectively.

$C_{24}H_{24}O_6N_3SCl$ requires: C, 55.65 N, 4.67; N, 8.11; S, 6.19, Cl, 6.84.

Found: C, 54.49; H, 4.67; N, 7.83; S, 6.20, Cl, 5.18.

EXAMPLE 47

Phthalide 6-[D(—)α-aminophenylacetamido] penicillanate, Hydrochloride

Method 1

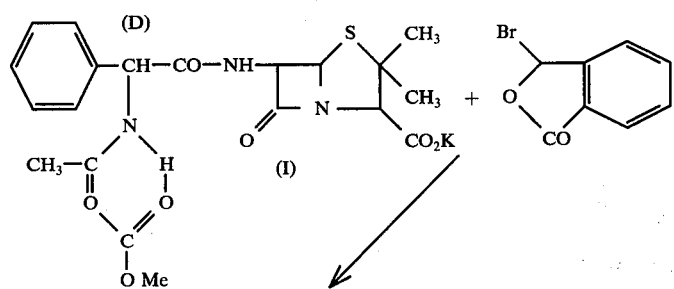

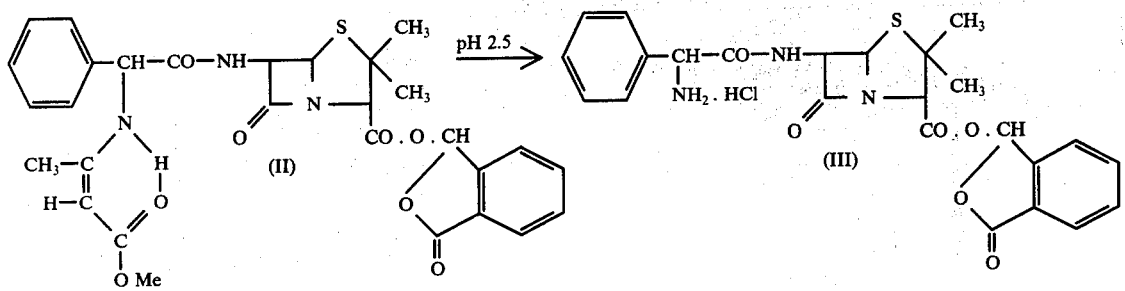

A fine suspension of potassium salt of enamine protected ampicillin I (25.18 g; 0.05 M) and 3-bromophthalide(10.65 g 0.05 M) were reacted in a 1:2 mixture of acetone/ethyl acetate.(1500 ml) for 24 hours. After filtration the organic layer was washed twice with 250ml. portions of 1N sodium bicarbonate and brine, dried over anhydrous magnesium sulphate and concentrated in vacuo. Addition of ether crystallised the phthalide enamine protected α-aminophenylacetamido penicillanate (II) in 85% yield. n.m.r. [(CD$_3$)$_2$SO] · δ = 7.86 (4H.m. phthalide aromatics); δ = 7.60 (1H.s. CO-.O.CH); δ = 7.35 (5H.s. aromatics ( δ = 5.30 - 5.65 (3H.m. β-lactams and α-proton): δ = 4.53 (1H.s. C—3 proton) δ = 4.50

(1H. s. —H)

δ = 3.56 (3H.s. O CH$_3$( δ = 1.78

(3H. s. CH$_3$—)

δ = 1.50 (6H.m. gemkdi CH$_3$). C$_{28}$H$_{29}$N$_3$O$_8$S requires: C, 59.26;
H, 5.11; N, 7.40 S, 5.68.
Found: C, 58.83; H, 5.00;1 1N, 6.89 S, 5.34.
Single spot on biochrematogram at R$_f$ = 0.95.

The enamine protecting group was removed from the product (II) by dissolving 10 g. in aqueous acetone (250 ml water to 250 ml acetone) and vigorously stirring this solution at pH 2.5 for 1 hour. The acetone was removed in vacuo and the ester (III), which was salted out of the aqueous phase as a sticky yellow gum, was dissolved in ethyl acetate (200 ml) and washed twice with 200 ml portion, of 1N sodium bicarbonate and brine and dried over anhydrous magensium sulphate. Careful addition of dry ester (ca.50 ml) to the dry ethyl acetate layer yielded the ampicillin phthalide ester as hydrochloride salt as a fine white amorphous solid in 80% yeild.
n.m.r. [(CD$_3$)$_2$ SO/D$_2$O): δ = 7.88 (4H.m. phthalide aromatics); δ = 7.60 (1H.s. CO.O CH-); δ = 7.48 (5/6H.m. aromatic) δm= 5.50 (2H.m. β-lactams); δ = 5.16 (1H.s. α-proton) δ = 4.54 (1H.s. C$_3$—proton) δ = 1.45 (6H.d. gem-dimethyls).
Purity as assessed by hydroxylamine assay = 110.3%.
Single spot on biochromatogram at R$_f$ = 0.85
C$_{24}$H$_{24}$N$_3$O$_6$SCl requires: C, 55.65;1H, 4.67; N, 8.11; S, 6.19.

Found: C, 54.60 H, 4.70; N, 7.92; S, 6.40.

METHOD 2

A mixture of acetone (250)ml. sodium D(—)N-methoxycarbonylpropen-2-yl-α-aminophenylacetate(30.5 g) ethyl chloroformate (10.9ml) and N-methylmorpholine (4-6 drops) were stirred together for 10-15 minutes at —20° to —30° C.

To this solution was added, all at once a solution of 6-APA (25.4 g) dissolved in water (50ml) within the aid of triethylamine (11.9 g) and then diluted with acetone (150 ml) and cooled to —20° C.

The reaction mixture was stirred for 45 mins. without further cooling and a solution of 3-bromophthalide (25 g) in acetone (100 ml) added all at once, after which stirring was continued for a further 5 hours, the temperature rising meanwhile to ambient (23° C.).

Acetone was next removed in vacuo, after first clarifying the mixture by filtration and to the residue was added ethyl acetate (375 ml.) and 2% sodium bicarbonate solution (200ml.). After stirring for a short while the phases were separated and the organic layer washed again with 2% sodium bicarbonate solution (200 ml).

To the ethyl acetate solution thus obtained was added water (375 ml) and 2N/HCl (60 ml) and this mixture stirred at ambient temperature (23° C) for 45 mins. Petrol (600 ml) was then added and after a short period of stirring the phases were allowed to separate. The organic layer was discarded and the aqueous layer was filtered with a little decolourising charcoal.

Sufficient sodium chloride to saturate the filtrate was next added and after a few minutes stirring the precipitated oil was extracted with methylene dichloride (1 × 400 ml, 1 × 100 ml). These extracts were combined, dried with anhydrous magnesium sulphate, filtered and evaporated under reduced pressure to approximately 100 ml. Ether (500 ml) was then added quickly, with stirring to the residue and the resulting precipitate stirred for about 30 mins, at ambient temperature. The product was filtered at the pump, washed with ether (2 × 50 ml) and dried for 3 hours in a forced-air oven at 35° - 40° C. The product was identical with an authenic sample of phthalide 6-[D(—)α-aminophenylacetamido] penicillanate.

EXAMPLE 48

Representative compounds made by the preceding Example were subjected to an experiment to determine their hydrolysis characteristics under various conditions. The results are tabulated below.

TABLE I
Esters of 6[D(—)α-aminophenylacetamido]penicillanic acid

| Product of Example | Percentage Hydrolysis to 6[D(—)α-aminophenylacetamido]penicillanic acid | | | | | | | | | | | |
|---|---|---|---|---|---|---|---|---|---|---|---|---|
| | Acid (pH 2.0) After (mins): | | | | Aqueous Buffer (pH 7.0) After (mins): | | | | Human blood (pH 7.0) After (mins): | | | |
| | 3 | 8 | 15 | 25 | 3 | 8 | 15 | 25 | 3 | 8 | 15 | 25 |
| 7 | 0 | 0 | 0 | 0 | 10 | 15 | 20 | 25 | 48 | 62 | 80 | 82 |
| 1 | 0 | 0 | 0 | 0 | 0 | 12 | 20 | 34 | 44 | 46 | 62 | 66 |
| 2 | 0 | 0 | 0 | 0 | 0 | 0 | 18 | 36 | 82 | 88 | 90 | 100 |
| 4 | 0 | 0 | 0 | 0 | 0 | 0 | 0 | 12 | 36 | 58 | 66 | 72 |
| 3 | 0 | 0 | 0 | 0 | 26 | 28 | 4.8 | 50 | 66 | 70 | 76 | 80 |
| 5 | 0 | 0 | 10 | 14 | 0 | 10 | 12 | 18 | 28 | 30 | 48 | 52 |
| 8 | 0 | 0 | 0 | 0 | 0 | 10 | 30 | 30 | 80 | 76 | 74 | 80 |

TABLE 2
Esters of Benzylpenicillin

| Product of Example | Percentage Hydrolysis to Benzylpenicillin at 37° C in : | | | | | | | |
|---|---|---|---|---|---|---|---|---|
| | Aqueous Buffer (pH 7.0) After (mins): | | | | Human Blood (pH 7.0) After (mins): | | | |
| | 3 | 8 | 15 | 25 | 3 | 8 | 15 | 25 |
| 46 | 0 | 12 | 16 | 34 | 87 | 92 | 100 | 100 |
| 15 | 0 | 0 | 0 | 0 | 0 | 0 | 16 | 40 |
| 10 | 0 | 0 | 0 | 0 | 74 | 68 | 66 | 62 |
| 11 | 28 | 36 | 42 | 52 | 66 | 72 | 78 | 80 |
| 45 | 0 | 0 | 0 | 0 | 22 | 32 | 38 | 38 |
| 12 | 0 | 0 | 12 | 22 | 60 | 68 | 78 | 84 |
| 13 | 0 | 10 | 16 | 28 | 18 | 46 | 52 | 60 |

TABLE 3
Esters of Phenoxymethylpenicillin

| Product of Example | Percentage Hydrolysis to Phenoxymethylpenicillin at 37° C in: | | | | | | | | | | | |
|---|---|---|---|---|---|---|---|---|---|---|---|---|
| | Acid (pH 2.0) After (mins): | | | | Aqueous Buffer (pH 7.0) After (mins): | | | | Human Blood (pH 7.0) After (mins): | | | |
| | 3 | 8 | 15 | 25 | 3 | 8 | 15 | 25 | 3 | 8 | 15 | 25 |
| 44 | 0 | 0 | 0 | 0 | 0 | 0 | 24 | 26 | 68 | 76 | 78 | 80 |
| 14 | 24 | 40 | 48 | 56 | 0 | 0 | 24 | 26 | 66 | 80 | 88 | 92 |
| 17 | 0 | 0 | 0 | 0 | 0 | 0 | 0 | 0 | 0 | 0 | 0 | 40 |
| 21 | — | 10 | 10 | 10 | 0 | 0 | 10 | 12 | 0 | 0 | 0 | 0 |
| 20 | 34 | 50 | 56 | 52 | 30 | 56 | 60 | 64 | — | 58 | 58 | 58 |

TABLE 4
Miscellaneous Esters

| Product of Example | Percentage Hydrolysis to parent free acid at 37° C in: | | | | | | | | | | | |
|---|---|---|---|---|---|---|---|---|---|---|---|---|
| | Acid (pH 2.0) After (mins): | | | | Aqueous Buffer (pH 7.0) After (mins): | | | | Human Blood (pH 7.0) After (mins): | | | |
| | 3 | 8 | 15 | 25 | 3 | 8 | 15 | 25 | 3 | 8 | 15 | 25 |
| 31 | — | — | — | — | 0 | 0 | 0 | 0 | 0 | 36 | 60 | 62 |
| 34 | 0 | 0 | 0 | 0 | 0 | 0 | 14 | 20 | 92 | 90 | 84 | 80 |
| 42 | 0 | 0 | 0 | 0 | 0 | 0 | 0 | 0 | 39 | 40 | 45 | 48 |

I claim:

1. A compound of formula (I) or a pharmaceutically acceptable acid addition salt of said compound having a basic nitrogen atom:

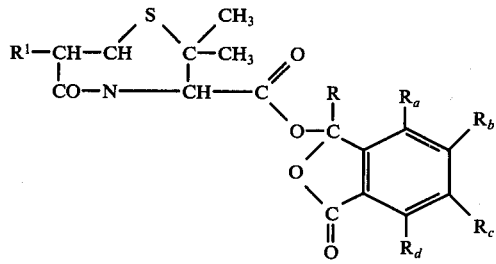

wherein R is hydrogen, methyl or phenyl; $R_a$, $R_b$, $R_c$ and $R_d$ are selected from hydrogen, lower alkyl, lower alkoxy, halo and nitro; $R^1$ is an antibacterially active penicillin-completing side chain selected from phenylacetamido, p-hydroxyphenylacetamido; p-heptylphenylacetamido; phenoxyacetamido; α-phenoxypropionamido; α-phenoxybutyramido; 2,6-dimethoxyphenylacetamido; 3-phenyl-5-methyl-isoxazole-4-carbamido; 3-(2-chlorophenyl)-5-methyl-isoxazole-4-carbamido; 3-(2,6-dichlorophenyl)-5-methyl-isoxazole-4-carbamido; 3-(2-chloro-6-fluorophenyl)-5-methyl-isoxazole-4-carbamido; 2-ethoxy-naphthyl-1-carbamido; o, m or p-aminophenylacetamido; 3-carboxy-quinoxalin-2-carbamido; 2-furylacetamido; 2-thienylacetamido; 3-thienylacetamido; 3-pyridylacetamido; isothiazolylacetamido; 3-hexenamide; 2-biphenylamido; n-hexanamido; n-octanamido; propionamido; α-aminophenylacetamido; α-amino-2-thienylacetamido; α-amino-3-thienylacetamido; α-methyl-aminophenylacetamido; α-amino-2- or -3- or -4-chlorophenylacetamido; α-amino-2-methoxyphenylacetamido; α-amino-2,4-dichlorophenylacetamido; α-amino-3,4-dichlorophenylacetamido; α-amino-α-methylphenylacetamido; α-amino-4-hydroxyphenylacetamido; α-amino-3-chloro-4-hydroxy-phenylacetamido; α-methylphenylacetamido; α-hydroxyphenylacetamido; α-carboxyphenylacetamido; α-(5-tetrazolyl)-phenylacetamido; α-quanidino-2-thienylacetamido; α-guanidino-4-hydroxyphenylacetamido α-guanidino-4-hydroxy-2- or -3-methylphenylacetamido; α-carboxy-3-thienylacetamido; α-sulphaminophenylacetamido; α-sulphamino- 3-thienylacetamido; α-(N-methylsulphamino)-phenylacetamido; α-azidophenylacetamido; 1-aminocyclohexylcarbamido; 1-aminocyclopentylcarbamido; 5-amino-5-carboxypentanamido; α-phenoxyphenylacetamido; α-phenyl-β-sulphaminopropionamido; α-sulphophenylacetamido; α-guanidinophenylacetamido; β-amino-β-cyclohexylpropionamido; α-(benzyloxycarbonyl)-phenylacetamido; or 2,2-dimethyl-5-oxo-4-phenyl-1-imidazolidinyl, (hexahydro-1H-azepin-1-yl)methyleneamino or N,N-dimethylformamidino, provided that when R is hydrogen and R¹ is D-α-aminophenylacetamido $R_a$, $R_b$, $R_c$ and $R_d$ are not all hydrogen.

2. The compound of claim 1 which is 5,6-dimethoxyphthalide 6[D(—)α-aminophenylacetamido] penicillanate or a pharmaceutically acceptable non-toxic acid addition salt thereof.

3. A compound of claim 1 wherein R¹ is phenylacetamido.

4. A compound of claim 1 wherein R¹ is phenoxymethylacetamido.

5. A compound of claim 1 wherein R¹ is α-aminophenylacetamido.

6. A compound of claim 1 wherein R¹ is α-guanidino-p-hydroxyphenylacetamido.

7. A compound of claim 1 wherein R¹ is α-carboxyphenylacetamido.

8. A compound of claim 1 wherein R¹ is α-azidophenylacetamido.

9. The compound of claim 1 which is 6-methoxyphthalide 6[D(—)α-aminophenylacetamido] penicillanate or a pharmaceutically acceptable acid addition salt thereof.

10. The compound of claim 1 which is 6-chlorophthalide 6[D(—)α-aminophenylacetamido] penicillanate or a pharmaceutically acceptable acid addition salt thereof.

11. The compound of claim 1 which is 4,5,6-trimethoxyphthalide 6[D(—)α-aminophenylacetamido] penicillanate or a pharmaceutically acceptable acid addition salt thereof.

12. The compound of claim 1 which is 6-bromophthalide 6[D(—)α-aminophenylacetamido] penicillanate or a pharmaceutically acceptable acid addition salt thereof.

13. The compound of claim 1 which is 3-methylphthalide 6[D(—)α-aminophenylacetamido] penicillanate or a pharmaceutically acceptable acid addition salt thereof.

14. The compound of claim 1 which is phthalide 6[D(—)α-amino-3-thienylacetamido] penicillanate or a pharmaceutically acceptable acid addition salt thereof.

15. The compound of claim 1 which is 5,6-dimethoxyphthalide 6[D,L-α-amino-3-thienylacetamido] penicillanate or a pharmaceutically acceptable acid addition salt thereof.

16. The compound of claim 1 which is 6-nitrophthalide 6[phenylacetamido] penicillanate.

17. The compound of claim 1 which is 5,6-dimethylphthalide 6[phenylacetamido] penicillanate.

18. The compound of claim 1 which is 6-methoxyphthalide 6[phenylacetamido] penicillanate.

19. The compound of claim 1 which is 3-phenylphthalide 6[phenylacetamido] penicillanate.

20. The compound of claim 1 which is 3-methylphthalide 6[phenylacetamido] penicillanate.

21. The compound of claim 1 which is 3-methylphthalide 6[phenoxyacetamido] penicillanate.

22. The compound of claim 1 which is 3-phenylphthalide 6[phenoxyacetamido] penicillanate.

23. The compound of claim 1 which is phthalide 6[D(—)α-guanidino-p-hydroxyphenylacetamido] penicillanate or a pharmaceutically acceptable acid addition salt thereof.

24. The compound of claim 1 which is phthalide 6[α-guanidino-4-hydroxy-3-methylphenylacetamido] penicillanate or a pharmaceutically acceptable acid addition salt thereof.

25. The compound of claim 1 which is phthalide 6[α-guanidino-4-hydroxy-2-methylphenylacetamido] penicillanate or a pharmaceutically acceptable acid addition salt thereof.

26. The compound of claim 1 which is phthalide 6[α-sulpho-phenylacetamido] penicillanate or a pharmaceutically acceptable acid addition salt thereof.

27. The compound of claim 1 which is phthalide 6[α-carboxy-phenylacetamido] penicillanate or a pharmaceutically acceptable acid addition salt thereof.

28. The compound of claim 1 which is α, β-bisphthalide 6[α-carboxyphenylacetamido]penicillanate.

29. The compound of claim 1 which is α, β-bisphthalide 6[α-carboxy-3-thienylacetamido]penicillanate.

30. The compound of claim 1 which is α-sulpho-phenylacetamido.

31. Phthalide 6[α-azido-phenylacetamido] penicillanate.

32. Phthalide 6[β-amino-β-cyclohex-3-enyl-propionamido] penicillanate or a pharmaceutically acceptable acid addition salt thereof;

33. Phthalide 6[-(3-o-chlorophenyl-5-methyl-isoxazole-4-carbamido] penicillanate.

34. Phthalide 6[D(—)α-amino-(p-hydroxyphenylacetamido] penicillanate or a pharmaceutically acceptable acid addition salt thereof.

35. Phthalide 6[(hexahydro-1H-azepin-1-yl)-methyleneamino] penicillante or a pharmaceutically acceptable acid addition salt thereof.

36. Phthalide 6-(N,N-dimethylformamidine-N¹-) penicillanate or a pharmaceutically acceptable acid addition salt thereof.

37. Phthalide 6[2,2-dimethyl-5-oxo-4-phenyl-1-imidazolidinyl] penicillanate.

* * * * *

UNITED STATES PATENT AND TRADEMARK OFFICE
CERTIFICATE OF CORRECTION

PATENT NO. : 4,036,829
DATED : July 19, 1977
INVENTOR(S) : Harry Ferres

It is certified that error appears in the above-identified patent and that said Letters Patent are hereby corrected as shown below:

Column 43, claim 1, the structural formula should read

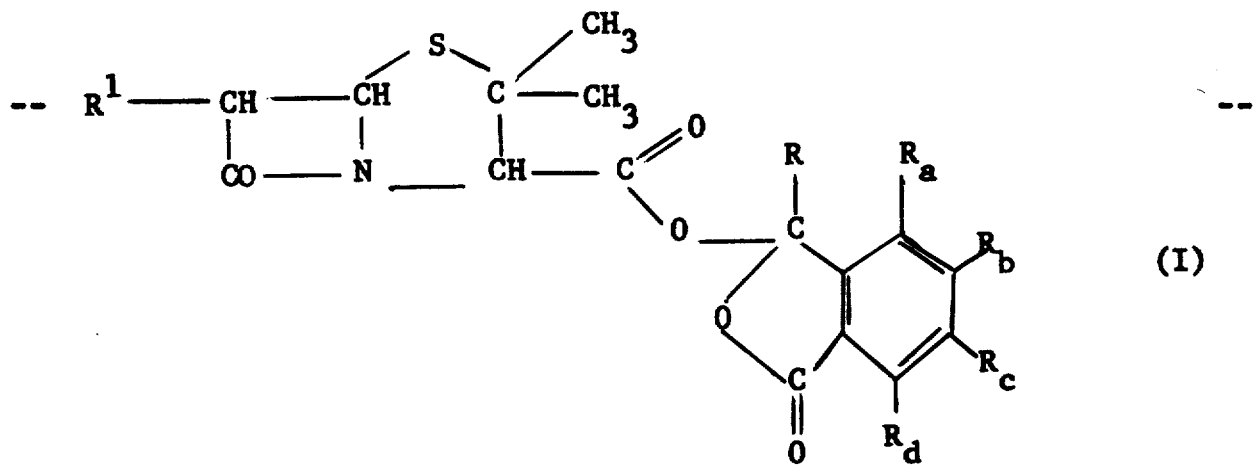

Signed and Sealed this

Twenty-second Day of November 1977

[SEAL]

Attest:

RUTH C. MASON
Attesting Officer

LUTRELLE F. PARKER
Acting Commissioner of Patents and Trademarks